US007214499B2

(12) United States Patent
Finlay et al.

(10) Patent No.: US 7,214,499 B2
(45) Date of Patent: May 8, 2007

(54) **PATHOGENIC *ESCHERICHIA COLI* ASSOCIATED PROTEIN**

(75) Inventors: B. Brett Finlay, Richmond (CA); Brendan Kenny, Redland (GB); Markus Stein, Quercegrossa (IT); Michael S. Donnenberg, Baltimore, MD (US); Li-Ching Lai, Upper Arlington, OH (US)

(73) Assignee: University of British Columbia (CA)

( * ) Notice: Subject to any disclaimer, the term of this patent is extended or adjusted under 35 U.S.C. 154(b) by 0 days.

(21) Appl. No.: 11/411,382

(22) Filed: Apr. 25, 2006

(65) Prior Publication Data

US 2006/0292180 A1    Dec. 28, 2006

Related U.S. Application Data

(62) Division of application No. 09/967,347, filed on Sep. 28, 2001, now Pat. No. 7,078,193, which is a division of application No. 09/171,517, filed as application No. PCT/CA97/00265 on Apr. 23, 1997, now Pat. No. 6,355,254.

(60) Provisional application No. 60/015,999, filed on Apr. 23, 1996.

(51) Int. Cl.
*G01N 33/554* (2006.01)
(52) U.S. Cl. .................. 435/7.32; 435/7.1; 530/387.1; 424/241.1
(58) Field of Classification Search ................. 435/7.1, 435/7.32; 530/387.1; 424/241.1
See application file for complete search history.

(56) References Cited

U.S. PATENT DOCUMENTS 6,090,623 A    7/2000  Harpold et al. ............. 435/369

FOREIGN PATENT DOCUMENTS

CA      2 078 716     3/1994
WO      WO 97 40063   10/1997

OTHER PUBLICATIONS

Abe et al., "Characterization of two virulence proteins secreted by rabbit enteropathogenic *Escherichia coli*, EspA and EspB, whose maximal expression is sensitive to host body temperature," *Infection and Immunity*, Sep. 1997, 65(9), 3547-3555.

Agin et al., *FEMS Microbiol. Lett.*, Nov. 1996, 144(2-3), 249-258.
Choi et al., *Mamm. Genome*, 1995, 6(9), 653-657.
Donnenberg, M.S., Submitted Oct. 9, 1995, GenBank Accession No. Z54352.
Ebel et al., *Infect. Immun.*, 1996, 64(11), 4472-4479.
Finlay et al., "Enterpathogenic *E. coli* exploitation of host epithelial cells," *Annals of New York Academy of Sciences*, 1996, 797, 26-31.
Jarvis et al., "Enteropathogenic *Escherichia coli* containsa putative type III secretion system necessary for the export of proteins involved in attaching and effacing lesion formation," *PNAS USA*, Aug. 15, 1998, 92(17), 7996-8000.
Jarvis et al., "Secretion of extracellular proteins by enterohemorrhagic *Escherichi coli* via a putative Type III secretion system," *Infection and Immunity*, Nov. 11, 1996, 64(11), 4826-4829.
Kenny et al., "EspA, a protein secreted by enterpathogenic *Escherichia coli* is required to induce signals in epithelial cells," *Molecular Microbiology*, 1996, 20(2), 313-323.
Kenny et al., "Protein secretion by enteropathogenic *Escherichia coli* is essential for transducing signals to epithelial cells," *PNAS USA*, Aug. 15, 1995, 92(17), 7991-7995.
Li et al., Human response to *Escherichia coli* O157:H7 infection: Antibodies to secreted virulence factors.
Murphy et al., "Somatic antigens of *Haemophilus influenzae* as vaccine components," *Pediatr. Infec. Dis. J.*, 1989, 8, S66-S68.
Mikayama et al., *Proc. Natl. Acad. Sci. USA*, Nov. 1993, 90, 10056-10060.
Rudinger et al., *Peptide Hormones Biol. Council*, Jun. 1976, 5-7.
Yamanka et al., "Antibody response to outer membrane protein of nontypeable *Haemophilus influenzae* in otitis-prone children,"*J. Pediatrics*, 1993, 122(2), 212-218.
Abe, A. et al., "*Escherichia coli* secreted protein Esp A (espA) gene," GenBank Accession No. U80908, 1997.
Abe, A. et al., "*Escherichia coli* secreted protein EspB (espB) gene," GenBank Accession No. U80796, 1997.
Donnenberg, M.S. et al., "*Escherichia coli* espB gene," GenBank Accession No. Z21555, 2000.
Ebel, F. et al., "*E. coli* espB gene," GenBank Accession No. X96953, 1997.
Kohler et al., "Continuous cultures of fused cells secreting antibody of predefined specificity," *Nature*, 1975, 256(495).
Kresse, A.U. et al., "*E. coli* espB gene," GenBank Accession No. X99670, 1997.
Lai, L.C. et al., "*E. coli* espD gene," GenBank Accession No. Y09228, 1997.

*Primary Examiner*—Jennifer E. Graser
(74) *Attorney, Agent, or Firm*—Woodcock Washburn LLP

(57) ABSTRACT

The present invention provides a polypeptide, called EspA, which is secreted by pathogenic *E. coli*, such as the enteropathogenic (SPEC) and enterohemorrhagic (EHEC) *E. coli*. The invention also provides isolated nucleic acid sequences encoding EspA polypeptide, EspA peptides, a recombinant method for producing recombinant EspA, antibodies which bind to EspA, and a kit for the detection of EspA-producing *E. coli*.

4 Claims, 8 Drawing Sheets

SEQ ID NO:1    ttatagtttttgtcatgctaagaaagattatgaagaggtatatac ATG GAT ACA
SEQ ID NO:2                                                   M   D   T    3
TCA ACT ACA GCA TCA GTT GCT AGT GCG AAT GCG AGT ACT TCG ACA
 S   T   T   A   S   V   A   S   A   N   A   S   T   S   T   18
TCA ATG GCC TAT GAT TTA GGG AGC ATG TCG AAA GAT GAC GTT ATT
 S   M   A   Y   D   L   G   S   M   S   K   D   D   V   I   33
GAT CTA TTT AAT AAA CTC GGT GTT TTT CAG GCT GCA ATT CTC ATG
 D   L   F   N   K   L   G   V   F   Q   A   A   I   L   M   48
TTT GCC TAT ATG TAT CAG GCA CAA AGC GAT CTG TCG ATT GCA AAG
 F   A   Y   M   Y   Q   A   Q   S   D   L   S   I   A   K   63
TTT GCT GAT ATG AAT GAG GCA TCT AAG GAG TCA ACC ACT GCC CAA
 F   A   D   M   N   E   A   S   K   E   S   T   T   A   Q   78
AAA ATG GCT AAT CTT GTA GAT GCT AAA ATT GCT GAC GTT CAG AGT
 K   M   A   N   L   V   D   A   K   I   A   D   V   Q   S   93
AGC TCT GAC AAG AAT GCG AAA GCT CAA CTT CCT GAT GAA GTG ATT
 S   S   D   K   N   A   K   A   Q   L   P   D   E   V   I  108
TCA TAT ATA AAT GAT CCT CGC AAT GAC ATT ACA ATA AGT GGT ATT
 S   Y   I   N   D   P   R   N   D   I   T   I   S   G   I  123
GAC AAT ATA AAT GCT CAA TTA GGC GCT GGT GAT TTG CAA ACG GTG
 D   N   I   N   A   Q   L   G   A   G   D   L   Q   T   V  138
AAA GCA GCT ATT TCA GCT AAA GCG AAT AAT TTG ACA ACG ACG GTC
 K   A   A   I   S   A   K   A   N   N   L   T   T   T   V  153
AAT AAT AGC CAG GTT GAA ATA CAG CAA ATG TCA AAT ACG TTA AAC
 N   N   S   Q   V   E   I   Q   Q   M   S   N   T   L   N  168
CTA TTA ACG AGT GCA CGT TCT GAT ATG CAG TCA CTG CAA TAT AGA
 L   L   T   S   A   R   S   D   M   Q   S   L   Q   Y   R  183
ACT ATT TCA GGA ATA TCC CTT GGT AAA TAA ccggagataactATG
 T   I   S   G   I   S   L   G   K   *                      198

*Fig. 1*

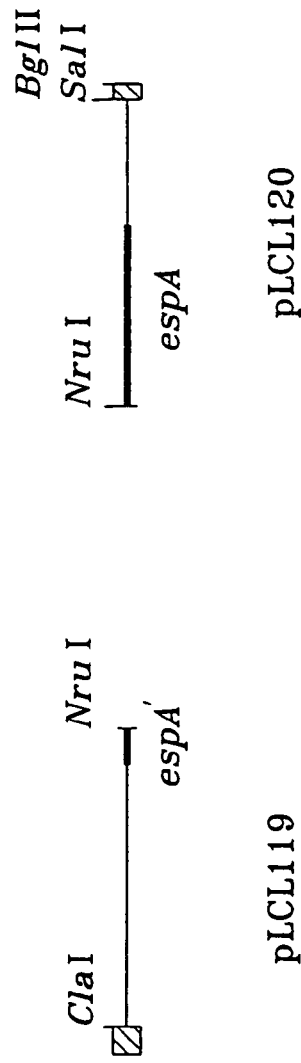
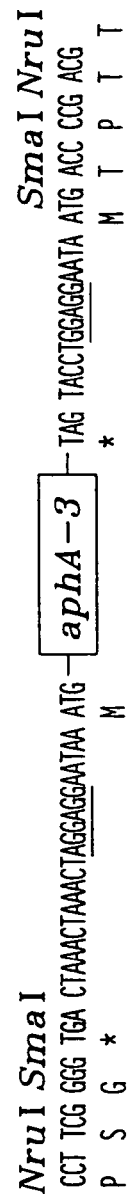
Fig. 2C
Fig. 2D

SEQ ID NO:3    ttaatgattggtaaagtaattgattataaggaggatgttatttgatattggtttttaat  60

SEQ ID NO:4    cgttttggtcttgctaagaaagattattaagagggtatatacATGGATACATCAACTGCA 120
                                                           M  D  T  S  T  A
ACATCAGTTGCTAGTGCGAACGCGAGTACTTCGACATCGACAGTCTATGACTTAGGCAGT 180
 T  S  V  A  S  A  N  A  S  T  S  T  S  T  V  Y  D  L  G  S
ATGTCGAAAGACGAAGTAGTTCAGCTATTTAATAAAGTCGGTGTTTTTCAGGCTGCGCTT 240
 M  S  K  D  E  V  V  Q  L  F  N  K  V  G  V  F  Q  A  A  L
CTCATGTTTGCCTATATGTATCAGGCACAAAGCGATCTGTCGATTGCAAAGTTTGCTGAT 300
 L  M  F  A  Y  M  Y  Q  A  Q  S  D  L  S  I  A  K  F  A  D
ATGAATGAGGCATCTAAGGAGTCAACCACAGCCCAAAAAATGGCTAATCTTGTGGATGCT 360
 M  N  E  A  S  K  E  S  T  T  A  Q  K  M  A  N  L  V  D  A
AAAATTGCTGATGTTCAGAGTAGTTCTGACAAGAATAAGAAAGCCAAACTTCCTCAAGAA 420
 K  I  A  D  V  Q  S  S  S  D  K  N  K  K  A  K  L  P  Q  E
GTGATTGACTATATAAATGATCCTCGCAATGACATTACAGTAAGTGGTATTAGCGATCTA 480
 V  I  D  Y  I  N  D  P  R  N  D  I  T  V  S  G  I  S  D  L
AATGCTGAATTAGGCGCTGGTGATTTGCAAACGGTGAAGGCCGCTATTTCGGCCAAATCG 540
 N  A  E  L  G  A  G  D  L  Q  T  V  K  A  A  I  S  A  K  S
AATAACTTGACCACGGTAGTGAATAATAGCCAGCTTGAAATACAGCAAATGTCAAATACG 600
 N  N  L  T  T  V  V  N  N  S  Q  L  E  I  Q  Q  M  S  N  T
TTAAACCTATTAACGAGTGCACGTTCTGATATTCAGTCACTGCAATACAGAACTATTTCA 660
 L  N  L  L  T  S  A  R  S  D  I  Q  S  L  Q  Y  R  T  I  S
GCAATATCCCTTGGTAAATAAccggagataactATGCTTAATGTAAATAGCGATATCCAG 720
 A  I  S  L  G  K  *             M  L  N  V  N  S  D  I  Q
TCTATG                                                       726
 S  M

Fig. 4A

SEQ ID NO:5
SEQ ID NO:6

```
tcgagtttaattattaaagagaatttaattATGAATACTATTGATTATACTAATCAAGTA  60
                              M  N  T  I  D  Y  T  N  Q  V
ATGACGGTTAATTCTGTTTCGGAGAATACTACCGGCTCTAATGCAATTACCGCATCTGCT 120
 M  T  V  N  S  V  S  E  N  T  T  G  S  N  A  I  T  A  S  A
ATTAATTCATCTTTGCTTACCGATGGTAAGGTCGATGTTTCTAAACTGATGCTGGAAATT 180
 I  N  S  S  L  L  T  D  G  K  V  D  V  S  K  L  M  L  E  I
CAAAAACTCCTGGGCAAGATGGTGCGTATATTGCAGGATTACCAACAGCAACAGTTGTCG 240
 Q  K  L  L  G  K  M  V  R  I  L  Q  D  Y  Q  Q  Q  Q  L  S
CAGAGCTATCAGATCCAACTGGCCGTTTTTGAGAGCCAGAATAAAGCCATTGATGAAAAA 300
 Q  S  Y  Q  I  Q  L  A  V  F  E  S  Q  N  K  A  I  D  E  K
AAGGCCGCTGCAACAGCCGCTCTGGTTGGTGGGGCTATTTCATCAGTATTGGGGATCTTA 360
 K  A  A  A  T  A  A  L  V  G  G  A  I  S  S  V  L  G  I  L
GGCTCTTTTGCAGCAATTAACAGTGCTACGAAAGGCGCGAGTGATATTGCTCAAAAAACC 420
 G  S  F  A  A  I  N  S  A  T  K  G  A  S  D  I  A  Q  K  T
GCCTCTACATCTTCTAAGGCTATTGATGCGGCTTCTGATACTGCGACTAAAACGTTGACT 480
 A  S  T  S  S  K  A  I  D  A  A  S  D  T  A  T  K  T  L  T
AAGGCAACGGAAAGCGTTGCTGATGCTGTTGAAGATGCATCCAGCGTGATGCAGCAAGCG 540
 K  A  T  E  S  V  A  D  A  V  E  D  A  S  S  V  M  Q  Q  A
ATGACTACAGCAACGAGAGCGGCCAGCCGTACATCCGACGTTGCTGATGACATTGCCGAT 600
 M  T  T  A  T  R  A  A  S  R  T  S  D  V  A  D  D  I  A  D
TCTGCTCAGAGAGCTTCTCAGCTGGCTGAAAACGCTGCAGATGCCGCTCAGAAGGCAAGT 660
 S  A  Q  R  A  S  Q  L  A  E  N  A  A  D  A  A  Q  K  A  S
CGGGCAAGCCGCTTTATGGCTGCAGTAGATAAGATTACTGGCTCTACACCATTTATTGCC 720
 R  A  S  R  F  M  A  A  V  D  K  I  T  G  S  T  P  F  I  A
GTTACCAGTCTTGCCGAAGGCACGAAGACATTGCCAACAACGGTATCTGAATCAGTCAAA 780
 V  T  S  L  A  E  G  T  K  T  L  P  T  T  V  S  E  S  V  K
TCTAACCATGAGATTAGCGAACAGCGTTATAAGTCTGTGGAGAACTTCCAGCAGGGTAAT 840
 S  N  H  E  I  S  E  Q  R  Y  K  S  V  E  N  F  Q  Q  G  N
TTGGATCTGTATAAGCAAGAAGTTCGCAGAGCGCAGGATGATATCGCTAGCCGTCTGCGT 900
 L  D  L  Y  K  Q  E  V  R  R  A  Q  D  D  I  A  S  R  L  R
GATATGACAACAGCCGCTCGCGATCTCACTGATCTTCAGAATCGTATGGGTCAATCGGTT 960
 D  M  T  T  A  A  R  D  L  T  D  L  Q  N  R  M  G  Q  S  V
CGCTTAGCTGGGTAAttgatcatggtcga                                989
 R  L  A  G  *
```

*Fig. 4B*

|          | EspA |  |
|---|---|---|
| SEQ ID NO:7 | RDEC-1    | MDTSTATSVASANASTSTSTVYDLGSMSKDEVVQLFNKVGVFQAALLMFA 50 |
| SEQ ID NO:8 | EPEC 0127 | MDTSTTASVASANASTSTSMAYDLGSMSKDDVIDLFNKLGVFQAATLMFA 50 |

|  | |
|---|---|
| RDEC-1    | YMYQAQSDLSIAKFADMNEASKESTTAQKMANLVDAKIADVQSSSPKNKK 100 |
| EPEC 0127 | YMYQAQSDLSIAKFADMNEASKESTTAQKMANLVDAKIADVQSSSDKNAK 100 |

|  | |
|---|---|
| RDEC-1    | AKLPQEVIDYINDPRNDITVSGISDLNAELGAGDLQTVKAAISAKSNNLT 150 |
| EPEC 0127 | AQLPDEVISYINDPRNDITISGIDNINAQLGAGDLQTVKAAISAKANNLT 150 |

|  | |
|---|---|
| REDEC-1   | TMVNNSQLEIQQMSNTLNLLTSARSDIQSLQYRTISAISLGK 192 |
| EPEC 0127 | TTVNNSQLEIQQMSNTLNLLTSARSDMQSLQYRTISGISLGK 192 |

*Fig. 4C*

|  |  | EspB |  |
|---|---|---|---|
| SEQ ID NO:9 | RDEC-1 | MNTIDYTNQVMIVNSVSENTTG-SNAITASA--INSSLLTDGKVDVSKLM | 47 |
| SEQ ID NO:10 | EHEC O26 | MNTIDYTNQVMIVNSVSENTTG-SNAITASA--INSSLLTDGKVDVSKLM | 47 |
| SEQ ID NO:11 | EHEC O157 | MNTIDNTIQVTMVNSASESTTGASSAVAASALSIDSSLLTDGKVDICKLM | 49 |
| SEQ ID NO:12 | EPEC O127 | MNTIDNNNAAIAVNSVLSSTTDSTSSTITSSISSSLLTDGRVDISKLL | 50 |

|  |  |  |
|---|---|---|
| RDEC-1 | LEIQKLLGKMVRILQDYQQQQLSQSYQIQLAVFESQNKAIDEKKAAATAA | 97 |
| EHEC O26 | LEIQKLLGKMVRILQDYQQQQLSQSYQIQLAVFESQNKAIDEKKAAATAA | 97 |
| EHEC O157 | LEIQKLLGKMVTLQDYQQKQLAQSYQIQQAVFESQNKAIEEKKAAATAA | 99 |
| EPEC O127 | LEVQKLLREMVTLQDYLQKQLAQSYDIQKAVFESQNKAIDEKKAGATAA | 100 |

|  |  |  |
|---|---|---|
| RDEC-1 | LVGGAISSVLGILGSFAAINSATKGASDIAQKTASTSSKAILAASDTATK | 147 |
| EHEC O26 | LVGGAISSVLGILGSFAAINSATKGASDIAQKTASTSSKAILAASDTATK | 147 |
| EHEC O157 | LVGGIISSALGILGSFAAMNNAAKGAGEIAEKASSASSKAAGAASEVANK | 149 |
| EPEC O127 | LIGGAISSVLGILGSFAAINSATKGASDVAQQAASTSAKSIGTVSEASTK | 150 |

|  |  |  |
|---|---|---|
| RDEC-1 | TLTKATESVADAVEDASSVMQQAMTTATRAASRTSDVADDIADSAQRASQ | 197 |
| EHEC O26 | TLTKATESVADAVEDASSVMQQAMTTATRAASRTSDVADDIADSAQRASQ | 197 |
| EHEC O157 | ALVKATESVADVAEEASSAHQKAMATTTKAASRASGVADDV---AF-KATD | 195 |
| EPEC O127 | ALAKASEGIADAADDAAGAMQQTIATAAKAASRTSGITDDVATSAQKASQ | 200 |

|  |  |  |
|---|---|---|
| RDEC-1 | LAENAADAAQKAS-R---ASRFMAAVDKITGSTPFIAVTSLAEGTKTLPT | 243 |
| EHEC O26 | LAENAADAAQKAS-R---ASRFMAAVDKITGSTPFIAVTSLAEGTKTLPT | 243 |
| EHEC O157 | FAEDLADAAEKTS-R---INKLLNSVDKLTNTTAFVAVTSLAEGTKTLPT | 241 |
| EPEC O127 | VAEFAADAAQELAQKAGLLSRFTAAAGRISGSTPFIVVTSLAEGTKTLPT | 250 |

|  |  |  |
|---|---|---|
| RDEC-1 | TVSESVKSNHEISEQRYKSVENFQQGNLDLYKQEVRRAQDDIASRLRDMT | 293 |
| EHEC O26 | TVSESVKSNHEISEQRYKSVENFQQGNLDLYKQEVRRAQDDIASRLRDMT | 293 |
| EHEC O157 | TISESVKSTHEVNEQRAKSLENFQQGNLELYKQDVRRTQDDITTRLRDIT | 291 |
| EPEC O127 | TISESVKSNHDINEQRAKSVENLQASNLDTYKQDVRRAQDDISSRLRDMT | 300 |

|  |  |  |
|---|---|---|
| RDEC-1 | TAARDLTDLQNRMGQSVRLAG | 314 |
| EHEC O26 | TAARDLTDLQNRMGQSVRLAG | 314 |
| EHEC O157 | SAVRDLLEVQNRMGQSGRLAG | 312 |
| EPEC O127 | TTARDLTDLINRMGQAARLAG | 321 |

|  |  | EspD |  |
|---|---|---|---|
| SEQ ID NO:13 | RDEC-1 | MLNVNSDIQSM | 11 |
| SEQ ID NO:14 | EPEC O127 | MLNVNNDIQSVRSGASAATATSGINQSEVTSALDLQLVKSTAPSASWTES | 50 |

Fig. 4D

SEQUENCE LISTING

<160> NUMBER OF SEQ ID NOS: 15

<210> SEQ ID NO 1
<211> LENGTH: 639
<212> TYPE: DNA
<213> ORGANISM: Escherichia coli
<220> FEATURE:
<221> NAME/KEY: CDS
<222> LOCATION: (46)..(624)

<400> SEQUENCE: 1

```
ttatagtttt tgtcatgcta agaaagatta tgaagaggta tatac atg gat aca tca      57
                                                  Met Asp Thr Ser
                                                   1 act aca gca tca gtt gct agt gcg aat gcg agt act tcg aca tca atg       105
Thr Thr Ala Ser Val Ala Ser Ala Asn Ala Ser Thr Ser Thr Ser Met
 5                  10                  15                  20 gcc tat gat tta ggg agc atg tcg aaa gat gac gtt att gat cta ttt       153
Ala Tyr Asp Leu Gly Ser Met Ser Lys Asp Asp Val Ile Asp Leu Phe
                 25                  30                  35 aat aaa ctc ggt gtt ttt cag gct gca att ctc atg ttt gcc tat atg       201
Asn Lys Leu Gly Val Phe Gln Ala Ala Ile Leu Met Phe Ala Tyr Met
         40                  45                  50 tat cag gca caa agc gat ctg tcg att gca aag ttt gct gat atg aat       249
Tyr Gln Ala Gln Ser Asp Leu Ser Ile Ala Lys Phe Ala Asp Met Asn
     55                  60                  65 gag gca tct aag gag tca acc act gcc caa aaa atg gct aat ctt gta       297
Glu Ala Ser Lys Glu Ser Thr Thr Ala Gln Lys Met Ala Asn Leu Val
 70                  75                  80 gat gct aaa att gct gac gtt cag agt agc tct gac aag aat gcg aaa       345
Asp Ala Lys Ile Ala Asp Val Gln Ser Ser Ser Asp Lys Asn Ala Lys
85                  90                  95                 100 gct caa ctt cct gat gaa gtg att tca tat ata aat gat cct cgc aat       393
Ala Gln Leu Pro Asp Glu Val Ile Ser Tyr Ile Asn Asp Pro Arg Asn
                105                 110                 115 gac att aca ata agt ggt att gac aat ata aat gct caa tta ggc gct       441
Asp Ile Thr Ile Ser Gly Ile Asp Asn Ile Asn Ala Gln Leu Gly Ala
            120                 125                 130 ggt gat ttg caa acg gtg aaa gca gct att tca gct aaa gcg aat aat       489
Gly Asp Leu Gln Thr Val Lys Ala Ala Ile Ser Ala Lys Ala Asn Asn
        135                 140                 145 ttg aca acg acg gtc aat aat agc cag ctt gaa ata cag caa atg tca       537
Leu Thr Thr Thr Val Asn Asn Ser Gln Leu Glu Ile Gln Gln Met Ser
    150                 155                 160 aat acg tta aac cta tta acg agt gca cgt tct gat atg cag tca ctg       585
Asn Thr Leu Asn Leu Leu Thr Ser Ala Arg Ser Asp Met Gln Ser Leu
165                 170                 175                 180 caa tat aga act att tca gga ata tcc ctt ggt aaa taa ccggacataa        634
Gln Tyr Arg Thr Ile Ser Gly Ile Ser Leu Gly Lys
                185                 190 ctatg                                                                  639
```

<210> SEQ ID NO 2
<211> LENGTH: 192
<212> TYPE: PRT
<213> ORGANISM: Escherichia coli

<400> SEQUENCE: 2

```
Met Asp Thr Ser Thr Thr Ala Ser Val Ala Ser Ala Asn Ala Ser Thr
 1               5                   10                  15
```

```
Ser Thr Ser Met Ala Tyr Asp Leu Gly Ser Met Ser Lys Asp Asp Val
            20                  25                  30

Ile Asp Leu Phe Asn Lys Leu Gly Val Phe Gln Ala Ala Ile Leu Met
            35                  40                  45

Phe Ala Tyr Met Tyr Gln Ala Gln Ser Asp Leu Ser Ile Ala Lys Phe
 50                  55                  60

Ala Asp Met Asn Glu Ala Ser Lys Glu Ser Thr Thr Ala Gln Lys Met
 65                  70                  75                  80

Ala Asn Leu Val Asp Ala Lys Ile Ala Asp Val Gln Ser Ser Ser Asp
                 85                  90                  95

Lys Asn Ala Lys Ala Gln Leu Pro Asp Glu Val Ile Ser Tyr Ile Asn
             100                 105                 110

Asp Pro Arg Asn Asp Ile Thr Ile Ser Gly Ile Asp Asn Ile Asn Ala
             115                 120                 125

Gln Leu Gly Ala Gly Asp Leu Gln Thr Val Lys Ala Ala Ile Ser Ala
     130                 135                 140

Lys Ala Asn Asn Leu Thr Thr Thr Val Asn Asn Ser Gln Leu Glu Ile
145                 150                 155                 160

Gln Gln Met Ser Asn Thr Leu Asn Leu Leu Thr Ser Ala Arg Ser Asp
                 165                 170                 175

Met Gln Ser Leu Gln Tyr Arg Thr Ile Ser Gly Ile Ser Leu Gly Lys
             180                 185                 190

<210> SEQ ID NO 3
<211> LENGTH: 726
<212> TYPE: DNA
<213> ORGANISM: Escherichia coli
<220> FEATURE:
<221> NAME/KEY: CDS
<222> LOCATION: (103)..(681)

<400> SEQUENCE: 3
ttaatgattg gtaaagtaat tgattataag gaggatgtta tttgatattg gtttttaat      60 cgttttggt cttgctaaga aagattatta agaggtatat ac atg gat aca tca       114
                                              Met Asp Thr Ser
                                                1 act gca aca tca gtt gct agt gcg aac gcg agt act tcg aca tcg aca    162
Thr Ala Thr Ser Val Ala Ser Ala Asn Ala Ser Thr Ser Thr Ser Thr
  5                  10                  15                  20 gtc tat gac tta ggc agt atg tcg aaa gac gaa gta gtt cag cta ttt    210
Val Tyr Asp Leu Gly Ser Met Ser Lys Asp Glu Val Val Gln Leu Phe
                 25                  30                  35 aat aaa gtc ggt gtt ttt cag gct gcg ctt ctc atg ttt gcc tat atg    258
Asn Lys Val Gly Val Phe Gln Ala Ala Leu Leu Met Phe Ala Tyr Met
             40                  45                  50 tat cag gca caa agc gat ctg tcg att gca aag ttt gct gat atg aat    306
Tyr Gln Ala Gln Ser Asp Leu Ser Ile Ala Lys Phe Ala Asp Met Asn
 55                  60                  65 gag gca tct aag gag tca acc aca gcc caa aaa atg gct aat ctt gtg    354
Glu Ala Ser Lys Glu Ser Thr Thr Ala Gln Lys Met Ala Asn Leu Val
 70                  75                  80 gat gct aaa att gct gat gtt cag agt agt tct gac aag aat aag aaa    402
Asp Ala Lys Ile Ala Asp Val Gln Ser Ser Ser Asp Lys Asn Lys Lys
 85                  90                  95                 100 gcc aaa ctt cct caa gaa gtg att gac tat ata aat gat cct cgc aat    450
Ala Lys Leu Pro Gln Glu Val Ile Asp Tyr Ile Asn Asp Pro Arg Asn
                 105                 110                 115
```

```
gac att aca gta agt ggt att agc gat cta aat gct gaa tta ggc gct    498
Asp Ile Thr Val Ser Gly Ile Ser Asp Leu Asn Ala Glu Leu Gly Ala
        120                 125                 130 ggt gat ttg caa acg gtg aag gcc gct att tcg gcc aaa tcg aat aac    546
Gly Asp Leu Gln Thr Val Lys Ala Ala Ile Ser Ala Lys Ser Asn Asn
            135                 140                 145 ttg acc acg gta gtg aat aat agc cag ctt gaa ata cag caa atg tca    594
Leu Thr Thr Val Val Asn Asn Ser Gln Leu Glu Ile Gln Gln Met Ser
150                 155                 160 aat acg tta aac cta tta acg agt gca cgt tct gat att cag tca ctg    642
Asn Thr Leu Asn Leu Leu Thr Ser Ala Arg Ser Asp Ile Gln Ser Leu
165                 170                 175                 180 caa tac aga act att tca gca ata tcc ctt ggt aaa taa ccggagataa    691
Gln Tyr Arg Thr Ile Ser Ala Ile Ser Leu Gly Lys
                185                 190 ctatgcttaa tgtaaatagc gatatccagt ctatg                              726
```

```
<210> SEQ ID NO 4
<211> LENGTH: 192
<212> TYPE: PRT
<213> ORGANISM: Escherichia coli

<400> SEQUENCE: 4
```

Met Asp Thr Ser Thr Ala Thr Ser Val Ala Ser Ala Asn Ala Ser Thr
1               5                   10                  15

Ser Thr Ser Thr Val Tyr Asp Leu Gly Ser Met Ser Lys Asp Glu Val
            20                  25                  30

Val Gln Leu Phe Asn Lys Val Gly Val Phe Gln Ala Ala Leu Leu Met
        35                  40                  45

Phe Ala Tyr Met Tyr Gln Ala Gln Ser Asp Leu Ser Ile Ala Lys Phe
    50                  55                  60

Ala Asp Met Asn Glu Ala Ser Lys Glu Ser Thr Thr Ala Gln Lys Met
65                  70                  75                  80

Ala Asn Leu Val Asp Ala Lys Ile Ala Asp Val Gln Ser Ser Ser Asp
                85                  90                  95

Lys Asn Lys Lys Ala Lys Leu Pro Gln Glu Val Ile Asp Tyr Ile Asn
            100                 105                 110

Asp Pro Arg Asn Asp Ile Thr Val Ser Gly Ile Ser Asp Leu Asn Ala
        115                 120                 125

Glu Leu Gly Ala Gly Asp Leu Gln Thr Val Lys Ala Ala Ile Ser Ala
    130                 135                 140

Lys Ser Asn Asn Leu Thr Thr Val Val Asn Asn Ser Gln Leu Glu Ile
145                 150                 155                 160

Gln Gln Met Ser Asn Thr Leu Asn Leu Leu Thr Ser Ala Arg Ser Asp
                165                 170                 175

Ile Gln Ser Leu Gln Tyr Arg Thr Ile Ser Ala Ile Ser Leu Gly Lys
            180                 185                 190

```
<210> SEQ ID NO 5
<211> LENGTH: 989
<212> TYPE: DNA
<213> ORGANISM: Escherichia coli
<220> FEATURE:
<221> NAME/KEY: CDS
<222> LOCATION: (31)..(975)

<400> SEQUENCE: 5
tcgagtttaa ttattaaaga gaatttaatt atg aat act att gat tat act aat    54
                                 Met Asn Thr Ile Asp Tyr Thr Asn
```

-continued

```
                     1               5
caa gta atg acg gtt aat tct gtt tcg gag aat act acc ggc tct aat    102
Gln Val Met Thr Val Asn Ser Val Ser Glu Asn Thr Thr Gly Ser Asn
         10              15                  20 gca att acc gca tct gct att aat tca tct ttg ctt acc gat ggt aag    150
Ala Ile Thr Ala Ser Ala Ile Asn Ser Ser Leu Leu Thr Asp Gly Lys
 25              30                  35                  40 gtc gat gtt tct aaa ctg atg ctg gaa att caa aaa ctc ctg ggc aag    198
Val Asp Val Ser Lys Leu Met Leu Glu Ile Gln Lys Leu Leu Gly Lys
                 45                  50                  55 atg gtg cgt ata ttg cag gat tac caa cag caa cag ttg tcg cag agc    246
Met Val Arg Ile Leu Gln Asp Tyr Gln Gln Gln Gln Leu Ser Gln Ser
             60                  65                  70 tat cag atc caa ctg gcc gtt ttt gag agc cag aat aaa gcc att gat    294
Tyr Gln Ile Gln Leu Ala Val Phe Glu Ser Gln Asn Lys Ala Ile Asp
         75                  80                  85 gaa aaa aag gcc gct gca aca gcc gct ctg gtt ggt ggg gct att tca    342
Glu Lys Lys Ala Ala Ala Thr Ala Ala Leu Val Gly Gly Ala Ile Ser
 90                  95                 100 tca gta ttg ggg atc tta ggc tct ttt gca gca att aac agt gct acg    390
Ser Val Leu Gly Ile Leu Gly Ser Phe Ala Ala Ile Asn Ser Ala Thr
105                 110                 115                 120 aaa ggc gcg agt gat att gct caa aaa acc gcc tct aca tct tct aag    438
Lys Gly Ala Ser Asp Ile Ala Gln Lys Thr Ala Ser Thr Ser Ser Lys
                125                 130                 135 gct att gat gcg gct tct gat act gcg act aaa acg ttg act aag gca    486
Ala Ile Asp Ala Ala Ser Asp Thr Ala Thr Lys Thr Leu Thr Lys Ala
            140                 145                 150 acg gaa agc gtt gct gat gct gtt gaa gat gca tcc agc gtg atg cag    534
Thr Glu Ser Val Ala Asp Ala Val Glu Asp Ala Ser Ser Val Met Gln
                155                 160                 165 caa gcg atg act aca gca acg aga gcg gcc agc cgt aca tcc gac gtt    582
Gln Ala Met Thr Thr Ala Thr Arg Ala Ala Ser Arg Thr Ser Asp Val
        170                 175                 180 gct gat gac att gcc gat tct gct cag aga gct tct cag ctg gct gaa    630
Ala Asp Asp Ile Ala Asp Ser Ala Gln Arg Ala Ser Gln Leu Ala Glu
185                 190                 195                 200 aac gct gca gat gcc gct cag aag gca agt cgg gca agc cgc ttt atg    678
Asn Ala Ala Asp Ala Ala Gln Lys Ala Ser Arg Ala Ser Arg Phe Met
                205                 210                 215 gct gca gta gat aag att act ggc tct aca cca ttt att gcc gtt acc    726
Ala Ala Val Asp Lys Ile Thr Gly Ser Thr Pro Phe Ile Ala Val Thr
            220                 225                 230 agt ctt gcc gaa ggc acg aag aca ttg cca aca acg gta tct gaa tca    774
Ser Leu Ala Glu Gly Thr Lys Thr Leu Pro Thr Thr Val Ser Glu Ser
        235                 240                 245 gtc aaa tct aac cat gag att agc gaa cag cgt tat aag tct gtg gag    822
Val Lys Ser Asn His Glu Ile Ser Glu Gln Arg Tyr Lys Ser Val Glu
250                 255                 260 aac ttc cag cag ggt aat ttg gat ctg tat aag caa gaa gtt cgc aga    870
Asn Phe Gln Gln Gly Asn Leu Asp Leu Tyr Lys Gln Glu Val Arg Arg
265                 270                 275                 280 gcg cag gat gat atc gct agc cgt ctg cgt gat atg aca aca gcc gct    918
Ala Gln Asp Asp Ile Ala Ser Arg Leu Arg Asp Met Thr Thr Ala Ala
                285                 290                 295 cgc gat ctc act gat ctt cag aat cgt atg ggt caa tcg gtt cgc tta    966
Arg Asp Leu Thr Asp Leu Gln Asn Arg Met Gly Gln Ser Val Arg Leu
            300                 305                 310 gct ggg taa ttgatcatgg tcga                                        989
Ala Gly
```

Ala Gly

<210> SEQ ID NO 6
<211> LENGTH: 314
<212> TYPE: PRT
<213> ORGANISM: Escherichia coli

<400> SEQUENCE: 6

```
Met Asn Thr Ile Asp Tyr Thr Asn Gln Val Met Thr Val Asn Ser Val
1               5                   10                  15

Ser Glu Asn Thr Thr Gly Ser Asn Ala Ile Thr Ala Ser Ala Ile Asn
            20                  25                  30

Ser Ser Leu Leu Thr Asp Gly Lys Val Asp Val Ser Lys Leu Met Leu
        35                  40                  45

Glu Ile Gln Lys Leu Leu Gly Lys Met Val Arg Ile Leu Gln Asp Tyr
    50                  55                  60

Gln Gln Gln Gln Leu Ser Gln Ser Tyr Gln Ile Gln Leu Ala Val Phe
65                  70                  75                  80

Glu Ser Gln Asn Lys Ala Ile Asp Glu Lys Ala Ala Ala Thr Ala
                85                  90                  95

Ala Leu Val Gly Gly Ala Ile Ser Ser Val Leu Gly Ile Leu Gly Ser
                100                 105                 110

Phe Ala Ala Ile Asn Ser Ala Thr Lys Gly Ala Ser Asp Ile Ala Gln
            115                 120                 125

Lys Thr Ala Ser Thr Ser Ser Lys Ala Ile Asp Ala Ala Ser Asp Thr
130                 135                 140

Ala Thr Lys Thr Leu Thr Lys Ala Thr Glu Ser Val Ala Asp Ala Val
145                 150                 155                 160

Glu Asp Ala Ser Ser Val Met Gln Gln Ala Met Thr Thr Ala Thr Arg
                165                 170                 175

Ala Ala Ser Arg Thr Ser Asp Val Ala Asp Asp Ile Ala Asp Ser Ala
            180                 185                 190

Gln Arg Ala Ser Gln Leu Ala Glu Asn Ala Ala Asp Ala Ala Gln Lys
        195                 200                 205

Ala Ser Arg Ala Ser Arg Phe Met Ala Ala Val Asp Lys Ile Thr Gly
    210                 215                 220

Ser Thr Pro Phe Ile Ala Val Thr Ser Leu Ala Glu Gly Thr Lys Thr
225                 230                 235                 240

Leu Pro Thr Thr Val Ser Glu Ser Val Lys Ser Asn His Glu Ile Ser
                245                 250                 255

Glu Gln Arg Tyr Lys Ser Val Glu Asn Phe Gln Gln Gly Asn Leu Asp
            260                 265                 270

Leu Tyr Lys Gln Glu Val Arg Arg Ala Gln Asp Asp Ile Ala Ser Arg
        275                 280                 285

Leu Arg Asp Met Thr Thr Ala Ala Arg Asp Leu Thr Asp Leu Gln Asn
    290                 295                 300

Arg Met Gly Gln Ser Val Arg Leu Ala Gly
305                 310
```

<210> SEQ ID NO 7
<211> LENGTH: 194
<212> TYPE: PRT
<213> ORGANISM: Escherichia coli

<400> SEQUENCE: 7

Met Asp Thr Ser Thr Ala Thr Ser Val Ala Ser Ala Asn Ala Ser Thr

```
              1               5                  10                 15
Ser Thr Ser Thr Val Tyr Asp Leu Gly Ser Met Ser Lys Asp Glu Val
                20                 25                 30

Val Gln Leu Phe Asn Lys Val Gly Val Phe Gln Ala Ala Leu Leu Met
                35                 40                 45

Phe Ala Tyr Met Tyr Gln Ala Gln Ser Asp Leu Ser Ile Ala Lys Phe
            50                 55                 60

Ala Asp Met Asn Glu Ala Ser Lys Glu Ser Thr Thr Ala Gln Lys Met
65                  70                 75                  80

Ala Asn Leu Val Asp Ala Lys Ile Ala Asp Val Gln Ser Ser Ser Asp
                85                 90                 95

Lys Asn Lys Lys Ala Lys Leu Pro Gln Glu Val Ile Asp Tyr Ile Asn
                100                105                110

Asp Pro Arg Asn Asp Ile Thr Val Ser Gly Ile Ser Asp Leu Asn Ala
            115                120                125

Glu Leu Gly Ala Gly Ala Gly Asp Leu Gln Thr Val Lys Ala Ala Ile
            130                135                140

Ser Ala Lys Ser Asn Asn Leu Thr Thr Val Val Asn Asn Ser Gln Leu
145                 150                155                 160

Glu Ile Gln Gln Met Ser Asn Thr Leu Asn Leu Leu Thr Ser Ala Arg
                165                170                175

Ser Asp Ile Gln Ser Leu Gln Tyr Arg Thr Ile Ser Ala Ile Ser Leu
            180                185                190

Gly Lys

<210> SEQ ID NO 8
<211> LENGTH: 194
<212> TYPE: PRT
<213> ORGANISM: Escherichia coli

<400> SEQUENCE: 8

Met Asp Thr Ser Thr Thr Ala Ser Val Ala Ser Ala Asn Ala Ser Thr
1               5                  10                 15

Ser Thr Ser Met Ala Tyr Asp Leu Gly Ser Met Ser Lys Asp Asp Val
                20                 25                 30

Ile Asp Leu Phe Asn Lys Leu Gly Val Phe Gln Ala Ala Ile Leu Met
                35                 40                 45

Phe Ala Tyr Met Tyr Gln Ala Gln Ser Asp Leu Ser Ile Ala Lys Phe
            50                 55                 60

Ala Asp Met Asn Glu Ala Ser Lys Glu Ser Thr Thr Ala Gln Lys Met
65                  70                 75                  80

Ala Asn Leu Val Asp Ala Lys Ile Ala Asp Val Gln Ser Ser Ser Asp
                85                 90                 95

Lys Asn Ala Lys Ala Gln Leu Pro Asp Glu Val Ile Ser Tyr Ile Asn
                100                105                110

Asp Pro Arg Asn Asp Ile Thr Ile Ser Gly Ile Asp Asn Ile Asn Ala
            115                120                125

Gln Leu Gly Ala Gly Ala Gly Asp Leu Gln Thr Val Lys Ala Ala Ile
            130                135                140

Ser Ala Lys Ala Asn Asn Leu Thr Thr Val Asn Asn Ser Gln Leu
145                 150                155                 160

Glu Ile Gln Gln Met Ser Asn Thr Leu Asn Leu Leu Thr Ser Ala Arg
                165                170                175

Ser Asp Met Gln Ser Leu Gln Tyr Arg Thr Ile Ser Gly Ile Ser Leu
```

Gly Lys

<210> SEQ ID NO 9
<211> LENGTH: 314
<212> TYPE: PRT
<213> ORGANISM: Escherichia coli

<400> SEQUENCE: 9

Met Asn Thr Ile Asp Tyr Thr Asn Gln Val Met Thr Val Asn Ser Val
1               5                   10                  15

Ser Glu Asn Thr Thr Gly Ser Asn Ala Ile Thr Ala Ser Ala Ile Asn
            20                  25                  30

Ser Ser Leu Leu Thr Asp Gly Lys Val Asp Val Ser Lys Leu Met Leu
        35                  40                  45

Glu Ile Gln Lys Leu Leu Gly Lys Met Val Arg Ile Leu Gln Asp Tyr
50                  55                  60

Gln Gln Gln Gln Leu Ser Gln Ser Tyr Gln Ile Gln Leu Ala Val Phe
65                  70                  75                  80

Glu Ser Gln Asn Lys Ala Ile Asp Glu Lys Ala Ala Ala Thr Ala
                85                  90                  95

Ala Leu Val Gly Gly Ala Ile Ser Ser Val Leu Gly Ile Leu Gly Ser
                100                 105                 110

Phe Ala Ala Ile Asn Ser Ala Thr Lys Gly Ala Ser Asp Ile Ala Gln
            115                 120                 125

Lys Thr Ala Ser Thr Ser Ser Lys Ala Ile Asp Ala Ala Ser Asp Thr
130                 135                 140

Ala Thr Lys Thr Leu Thr Lys Ala Thr Glu Ser Val Ala Asp Ala Val
145                 150                 155                 160

Glu Asp Ala Ser Ser Val Met Gln Gln Ala Met Thr Thr Ala Thr Arg
                165                 170                 175

Ala Ala Ser Arg Thr Ser Asp Val Ala Asp Ile Ala Asp Ser Ala
            180                 185                 190

Gln Arg Ala Ser Gln Leu Ala Glu Asn Ala Ala Asp Ala Ala Gln Lys
            195                 200                 205

Ala Ser Arg Ala Ser Arg Phe Met Ala Ala Val Asp Lys Ile Thr Gly
210                 215                 220

Ser Thr Pro Phe Ile Ala Val Thr Ser Leu Ala Glu Gly Thr Lys Thr
225                 230                 235                 240

Leu Pro Thr Thr Val Ser Glu Ser Val Lys Ser Asn His Glu Ile Ser
                245                 250                 255

Glu Gln Arg Tyr Lys Ser Val Glu Asn Phe Gln Gln Gly Asn Leu Asp
            260                 265                 270

Leu Tyr Lys Gln Glu Val Arg Arg Ala Gln Asp Asp Ile Ala Ser Arg
        275                 280                 285

Leu Arg Asp Met Thr Thr Ala Ala Arg Asp Leu Thr Asp Leu Gln Asn
    290                 295                 300

Arg Met Gly Gln Ser Val Arg Leu Ala Gly
305                 310

<210> SEQ ID NO 10
<211> LENGTH: 314
<212> TYPE: PRT
<213> ORGANISM: Escherichia coli

<400> SEQUENCE: 10

-continued

```
Met Asn Thr Ile Asp Tyr Thr Asn Gln Val Met Thr Val Asn Ser Val
1               5                   10                  15

Ser Glu Asn Thr Thr Gly Ser Asn Ala Ile Thr Ala Ser Ala Ile Asn
            20                  25                  30

Ser Ser Leu Leu Thr Asp Gly Lys Val Asp Val Ser Lys Leu Met Leu
        35                  40                  45

Glu Ile Gln Lys Leu Leu Gly Lys Met Val Arg Ile Leu Gln Asp Tyr
    50                  55                  60

Gln Gln Gln Gln Leu Ser Gln Ser Tyr Gln Ile Gln Leu Ala Val Phe
65                  70                  75                  80

Glu Ser Gln Asn Lys Ala Ile Asp Glu Lys Ala Ala Thr Ala
                85                  90                  95

Ala Leu Val Gly Gly Ala Ile Ser Ser Val Leu Gly Ile Leu Gly Ser
            100                 105                 110

Phe Ala Ala Ile Asn Ser Ala Thr Lys Gly Ala Ser Asp Ile Ala Gln
            115                 120                 125

Lys Thr Ala Ser Thr Ser Ser Lys Ala Ile Asp Ala Ala Ser Asp Thr
    130                 135                 140

Ala Thr Lys Thr Leu Thr Lys Ala Thr Glu Ser Val Ala Asp Ala Val
145                 150                 155                 160

Glu Asp Ala Ser Ser Val Met Gln Gln Ala Met Thr Thr Ala Thr Arg
                165                 170                 175

Ala Ala Ser Arg Thr Ser Asp Val Ala Asp Asp Ile Ala Asp Ser Ala
            180                 185                 190

Gln Arg Ala Ser Gln Leu Ala Glu Asn Ala Ala Asp Ala Ala Gln Lys
    195                 200                 205

Ala Ser Arg Ala Ser Arg Phe Met Ala Ala Val Asp Lys Ile Thr Gly
210                 215                 220

Ser Thr Pro Phe Ile Ala Val Thr Ser Leu Ala Glu Gly Thr Lys Thr
225                 230                 235                 240

Leu Pro Thr Thr Val Ser Glu Ser Val Lys Ser Asn His Glu Ile Ser
                245                 250                 255

Glu Gln Arg Tyr Lys Ser Val Glu Asn Phe Gln Gln Gly Asn Leu Asp
            260                 265                 270

Leu Tyr Lys Gln Glu Val Arg Arg Ala Gln Asp Ile Ala Ser Arg
    275                 280                 285

Leu Arg Asp Met Thr Thr Ala Ala Arg Asp Leu Thr Asp Leu Gln Asn
290                 295                 300

Arg Met Gly Gln Ser Val Arg Leu Ala Gly
305                 310
```

<210> SEQ ID NO 11
<211> LENGTH: 312
<212> TYPE: PRT
<213> ORGANISM: Escherichia coli

<400> SEQUENCE: 11

```
Met Asn Thr Ile Asp Asn Thr Gln Val Thr Met Val Asn Ser Ala Ser
1               5                   10                  15

Glu Ser Thr Thr Gly Ala Ser Ser Ala Val Ala Ala Ser Ala Leu Ser
            20                  25                  30

Ile Asp Ser Ser Leu Leu Thr Asp Gly Lys Val Asp Ile Cys Lys Leu
        35                  40                  45

Met Leu Glu Ile Gln Lys Leu Leu Gly Lys Met Val Thr Leu Leu Gln
```

```
                50                  55                  60
Asp Tyr Gln Gln Lys Gln Leu Ala Gln Ser Tyr Gln Ile Gln Gln Ala
 65                  70                  75                  80

Val Phe Glu Ser Gln Asn Lys Ala Ile Glu Glu Lys Lys Ala Ala Ala
                 85                  90                  95

Thr Ala Ala Leu Val Gly Gly Ile Ile Ser Ala Leu Gly Ile Leu
                100                 105                 110

Gly Ser Phe Ala Ala Met Asn Asn Ala Ala Lys Gly Ala Gly Glu Ile
                115                 120                 125

Ala Glu Lys Ala Ser Ser Ala Ser Ser Lys Ala Ala Gly Ala Ala Ser
130                 135                 140

Glu Val Ala Asn Lys Ala Leu Val Lys Ala Thr Glu Ser Val Ala Asp
145                 150                 155                 160

Val Ala Glu Glu Ala Ser Ser Ala Met Gln Lys Ala Met Ala Thr Thr
                165                 170                 175

Thr Lys Ala Ala Ser Arg Ala Ser Gly Val Ala Asp Asp Val Ala Lys
                180                 185                 190

Ala Thr Asp Phe Ala Glu Asp Leu Ala Asp Ala Ala Glu Lys Thr Ser
                195                 200                 205

Arg Ile Asn Lys Leu Leu Asn Ser Val Asp Lys Leu Thr Asn Thr Thr
                210                 215                 220

Ala Phe Val Ala Val Thr Ser Leu Ala Glu Gly Thr Lys Thr Leu Pro
225                 230                 235                 240

Thr Thr Ile Ser Glu Ser Val Lys Ser Thr His Glu Val Asn Glu Gln
                245                 250                 255

Arg Ala Lys Ser Leu Glu Asn Phe Gln Gln Gly Asn Leu Glu Leu Tyr
                260                 265                 270

Lys Gln Asp Val Arg Arg Thr Gln Asp Ile Thr Thr Arg Leu Arg
                275                 280                 285

Asp Ile Thr Ser Ala Val Arg Asp Leu Leu Glu Val Gln Asn Arg Met
                290                 295                 300

Gly Gln Ser Gly Arg Leu Ala Gly
305                 310

<210> SEQ ID NO 12
<211> LENGTH: 321
<212> TYPE: PRT
<213> ORGANISM: Escherichia coli

<400> SEQUENCE: 12

Met Asn Thr Ile Asp Asn Asn Ala Ala Ile Ala Val Asn Ser Val
 1               5                  10                  15

Leu Ser Ser Thr Thr Asp Ser Thr Ser Thr Thr Ser Ala Ser
                 20                  25                  30

Ser Ile Ser Ser Leu Leu Thr Asp Gly Arg Val Asp Ile Ser Lys
                 35                  40                  45

Leu Met Leu Glu Val Gln Lys Leu Leu Arg Glu Met Val Thr Thr Leu
 50                  55                  60

Gln Asp Tyr Leu Gln Lys Gln Leu Ala Gln Ser Tyr Asp Ile Gln Lys
 65                  70                  75                  80

Ala Val Phe Glu Ser Gln Asn Lys Ala Ile Asp Glu Lys Lys Ala Gly
                 85                  90                  95

Ala Thr Ala Ala Leu Ile Gly Gly Ala Ile Ser Ser Val Leu Gly Ile
                100                 105                 110
```

-continued

```
Leu Gly Ser Phe Ala Ala Ile Asn Ser Ala Thr Lys Gly Ala Ser Asp
            115                 120                 125

Val Ala Gln Gln Ala Ala Ser Thr Ser Ala Lys Ser Ile Gly Thr Val
        130                 135                 140

Ser Glu Ala Ser Thr Lys Ala Leu Ala Lys Ala Ser Glu Gly Ile Ala
145                 150                 155                 160

Asp Ala Ala Asp Asp Ala Ala Gly Ala Met Gln Gln Thr Ile Ala Thr
                165                 170                 175

Ala Ala Lys Ala Ala Ser Arg Thr Ser Gly Ile Thr Asp Asp Val Ala
            180                 185                 190

Thr Ser Ala Gln Lys Ala Ser Gln Val Ala Glu Glu Ala Ala Asp Ala
        195                 200                 205

Ala Gln Glu Leu Ala Gln Lys Ala Gly Leu Leu Ser Arg Phe Met Ala
    210                 215                 220

Ala Ala Gly Arg Ile Ser Gly Ser Thr Pro Phe Ile Val Val Thr Ser
225                 230                 235                 240

Leu Ala Glu Gly Thr Lys Thr Leu Pro Thr Thr Ile Ser Glu Ser Val
                245                 250                 255

Lys Ser Asn His Asp Ile Asn Glu Gln Arg Ala Lys Ser Val Glu Asn
            260                 265                 270

Leu Gln Ala Ser Asn Leu Asp Leu Tyr Lys Gln Asp Val Arg Arg Ala
        275                 280                 285

Gln Asp Asp Ile Ser Ser Arg Leu Arg Asp Met Thr Thr Thr Ala Arg
    290                 295                 300

Asp Leu Thr Asp Leu Ile Asn Arg Met Gly Gln Ala Ala Arg Leu Ala
305                 310                 315                 320

Gly
```

<210> SEQ ID NO 13
<211> LENGTH: 11
<212> TYPE: PRT
<213> ORGANISM: Escherichia coli

<400> SEQUENCE: 13

```
Met Leu Asn Val Asn Ser Asp Ile Gln Ser Met
1               5                   10
```

<210> SEQ ID NO 14
<211> LENGTH: 50
<212> TYPE: PRT
<213> ORGANISM: Escherichia coli

<400> SEQUENCE: 14

```
Met Leu Asn Val Asn Asn Asp Ile Gln Ser Val Arg Ser Gly Ala Ser
1               5                   10                  15

Ala Ala Thr Ala Thr Ser Gly Ile Asn Gln Ser Glu Val Thr Ser Ala
            20                  25                  30

Leu Asp Leu Gln Leu Val Lys Ser Thr Ala Pro Ser Ala Ser Trp Thr
        35                  40                  45

Glu Ser
    50
```

<210> SEQ ID NO 15
<211> LENGTH: 856
<212> TYPE: DNA
<213> ORGANISM: Escherichia coli

<400> SEQUENCE: 15

-continued

```
ccttcggggt gactaaacta aactaggagg aataaatggc taaaatgaga atatcaccgg      60
aattgaaaaa actgatcgaa aaataccgct gcgtaaaaga tacggaagga atgtctcctg     120
ctaaggtata taagctggtg ggagaaaatg aaaacctata tttaaaaatg acggacagcc     180
ggtataaagg gaccacctat gatgtggaac gggaaaagga catgatgcta tggctggaag     240
gaaagctgcc tgttccaaag gtcctgcact ttgaacggca tgatggctgg agcaatctgc     300
tcatgagtga ggccgatggc gtcctttgct cggaagagta tgaagatgaa caaagccctg     360
aaaagattat cgagctgtat gcggagtgca tcaggctctt tcactccatc gacatatcgg     420
attgtcccta tacgaatagc ttagacagcc gcttagccga attggattac ttactgaata     480
acgatctggc cgatgtggat tgcgaaaact gggaagaaga cactccattt aaagatccgc     540
gcgagctgta tgattttttta aagacggaaa agcccgaaga ggaacttgtc ttttcccacg     600
gcgacctggg agacagcaac atctttgtga agatggcaa agtaagtggc tttattgatc     660
ttgggagaag cggcagggcg gacaagtggt atgacattgc cttctgcgtc cggtcgatca     720
gggaggatat cggggaagaa cagtatgtcg agctattttt tgacttactg gggatcaagc     780
ctgattggga gaaaataaaa tattatattt tactggatga attgttttag tacctggagg     840
aataatgacc ccgacg                                                     856
```

PATHOGENIC ESCHERICHIA COLI ASSOCIATED PROTEIN

CROSS-REFERENCE TO RELATED APPLICATION

This application is a divisional of application Ser. No. 09/967,347, filed Sep. 28, 2001, now U.S. Pat. No. 7,078,193; which is a divisional of application Ser. No. 09/171,517, filed Aug. 10, 1999, now U.S. Pat. No. 6,355,254; which is a 371 conversion application of international patent application PCT/CA97/00265, filed Apr. 23, 1997; which claims priority from U.S. Provisional Patent Application No. 60/015,999, filed Apr. 23, 1996. Each of the foregoing patents and applications is incorporated by reference herein in their entirety.

FIELD OF THE INVENTION

The present invention relates generally to the virulence of pathogenic organisms and more specifically to virulence factors associated with enteropathogenic bacteria.

BACKGROUND OF THE INVENTION

Antibiotics have been used for years to successfully treat diverse bacterial infections. However, bacterial resistance to antibiotics has been an increasing problem over the past few years. Many pathogens are now resistant to several antibiotics, and in some cases, the diseases they cause are no longer treatable with conventional antibiotics. Despite the past successes of antibiotics, there have been few, if any, new classes of antibiotics developed in the past two decades. New variations on existing drugs have been introduced, but resistance to these compounds usually arises within a short period of time.

Many studies have shown that if a mutation is made in a gene that encodes a virulence factor, the organism containing that gene is no longer pathogenic.

Additionally, if a host is vaccinated against a virulence factor, disease can often be blocked. However, it has not been shown that specific inhibition of a virulence factor can attenuate disease.

The mechanisms of action for toxins, adherence, invasion, intracellular parasitism, have been studied. However, each virulence factor uses a different mechanism, which has made the development of a broad spectrum inhibitor impossible. One conserved factor that could be considered a target for a therapeutic is a two-component regulatory system. However, this system is not specific for virulence factors, and is used in several bacterial housekeeping systems. Additionally, the systems have been identified in eukaryotic systems, which would increase the risk of host toxicity if an inhibitor was utilized. To develop an ideal anti-infective agent, the bacterial virulence mechanism that the antibiotic affects should be universal for many pathogens, specific for virulence mechanisms, and not be present in host cells. One such system that has recently been identified is the bacterial type III secretion system.

Gram-negative bacteria utilize specialized machinery to export molecules across their two membranes and the piroplasm, a process critical for moving virulence factors to the bacterial surface where they can interact with host components. Gramnegative secretion has been divided into four major pathways. First, the Type I secretion is used by a small family of toxins, with *E. coli* hemolysin being the prototype. Second, the type II secretion system is the major export pathway used by most Gram-negative bacteria to export many molecules, including some virulence factors; it shares homology to mammalian drug resistance mechanisms. Third, the type IV secretion system is encoded within the secreted product, which cleaves itself as part of the secretion mechanism; the prototype of this system is the *Neisseria* IgA protease. Fourth, the most recently discovered secretion pathway, is the type III pathway.

Type III secretion systems were originally described as a secretion system for *Yersinia* secreted virulence proteins, YOPs, which are critical for *Yersinia* virulence. A homologous secretion system was then identified in several plant pathogens, including *Pseudomonas syringae, P. solanacearurn*, and *Xantharnonas campestris*. These plant pathogens use this secretion pathway to secrete virulence factors (harpins and others) that are required for causing disease in plants. Although the secretion system is similar, harpins and YOPs (i.e., the secreted virulence factors) are not homologous polypeptides. Several other type III secretion systems necessary for virulence have more recently been identified in other pathogens. These systems include the invasion systems *Salmonella* and *Shigella* use to enter cells and cause disease. Another type III secretion system has been identified in *Salmonella* which is critical for disease, although the secreted products of this pathway and the virulence mechanisms have not been established yet. *Pseudomonas aeruginosa* has a type III secretion system necessary for secretion of Exoenzyme S, a potent virulence factor.

Enteropathogenic *Escherichia coli* (EPEC) is a leading cause of infant diarrhea and was the first *E. coli* shown to cause gastroenteritis. Enteropathogenic *E. coli* activates the host epithelial cells' signal transduction pathways and causes cytoskeletal rearrangement, along with pedestal and attaching/effacing lesion formation.

A three-stage model has described enteropathogenic *E. coli* pathogenesis. An initial localized adherence to epithelial cells, mediated by a type IV fimbria, is followed by the activation of host epithelial cell signal transduction pathways and intimate attachment to host epithelial cells. These final two steps are collectively known as attaching and effacing. The signal transduction in the host epithelial cells involves activation of host cell tyrosine kinase activity leading to tyrosine phosphorylation of a 90 kilodalton host membrane protein, Hp90, and fluxes of intracellular inositol phosphate($IP_3$) and calcium. Following this signal transduction, the bacteria adheres intimately to the surface of the epithelial cell, accompanied by damage to host epithelial cell microvilli and accumulation of cytoskeletal proteins beneath the bacteria.

SUMMARY OF THE INVENTION

The present invention is based on the discovery of a protein associated with virulence in pathogenic bacteria, for example enteropathogenic *E. coli*.

DNA sequence analysis of the Locus of Enterocyte Effacement between eaeA and espB identified a gene (espA) that matched the amino terminal sequence of the 25 kilodalton enteropathogenic *E. coli* secreted protein. A mutant with an insertion in espA does not secrete this protein, activate epithelial cell signal transduction or cause cytoskeletal rearrangement. However, these functions could be complemented by a cloned wild-type espA gene.

Two enteropathogenic *E. coli* genes, espA and espB, that encode secreted virulence factors, EspA and EspB respectively, were cloned and sequenced. These proteins were shown to be involved in the triggering of host epithelial signal transduction pathways and invasion. Since EspA is a secreted protein, it is ideally suited for use in a fusionprotein linked to a polypeptide of interest.

The type III secretion pathway is an ideal target for potential inhibitors, because it is a virulence factor-specific conserved pathway identified in bacteria. The present invention provides a method for identifying inhibitors of type III secretion systems. The relevance of this invention is directed toward the development of new antibacterial therapeutics. In contrast to other antibiotics, the compounds identified by the method of this invention will not kill or inhibit growth of pathogens; instead, the compounds will block the secretion of virulence factors that are critical to causing disease. Because the type III secretion system is the first virulence mechanism that shows a large degree of conservation between diverse pathogens, some of the compounds identified by the method of this invention will be broad spectrum therapeutics. The benefit would be the identification of new therapeutics that could be used in the treatment of several human, animal, and plant diseases.

BRIEF DESCRIPTION OF THE DRAWINGS

FIG. 1 shows the nucleotide and deduced amino acid sequence of espA (herein referred to as SEQ ID NO:1 and SEQ ID NO:2, respectively). Potential ribosome binding sites are underlined. Nucleotides included in primers Donne-99 and Donne-100, flanking the deletion engineered in pLCL121, are boxed.

FIGS. 2A, 2B, 2C and 2D (SEQ ID NO: 15) show the construction of a non-polar mutation in espA. Primers Donne-99 and the reverse primer were used to amplify a fragment containing a 5' portion of the gene, which was cloned into pCRscript to create pLCL119. Primers Donne-100 and the universal primer were used to amplify a fragment containing a 3' portion of the gene, which was cloned into pCRscript to create pLCL120. New NruI sites were incorporated into both Donne-99 and Donne-100 so that the NruI-SalI fragment of pLCL120 could be cloned into pLCL119 to create pLCL121, which has a 150 bp deletion within the espA gene. A SmaI fragment from pUC18K containing the aphA-3 kanamycin resistance gene was cloned into the NruI site of pLCL121 to create pLCL122. This insertion results in a transcriptional fusion of the aphA-3 gene and a translational fusion of the 3' end of the espA gene, with preservation of the espA reading frame. The ribosome binding sites are underlined.

FIGS. 4A, 4B, 4C and 4D show the nucleotide and predicted amino acid sequence of RDEC-1 espA (A) (herein referred to as SEQ ID NO: 3 and SEQ ID NO:4, respectively) and espB (B) (herein referred to as SEQ ID NO: 5 and SEQ ID NO:6, respectively). Asterisks indicate stop codons. Potential ribosome binding sites are underlined. Amino acid sequences from several *E. coli* strains of EspA are aligned in C (SEQ ID NOS:7–8), and EspB and EspD are aligned in D (SEQ ID NOS: 9–14). Boxed areas represent identity.

Figure 2A:
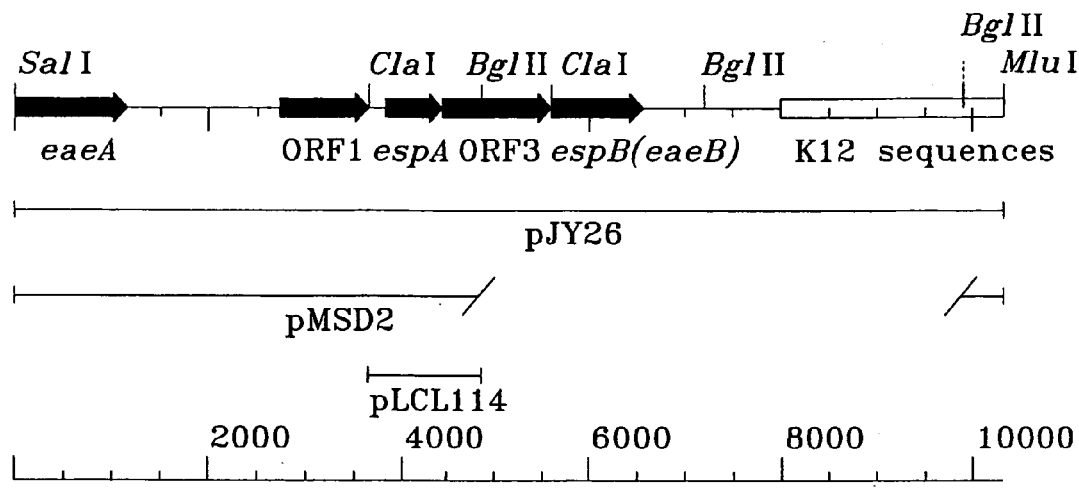
Figure 2B:
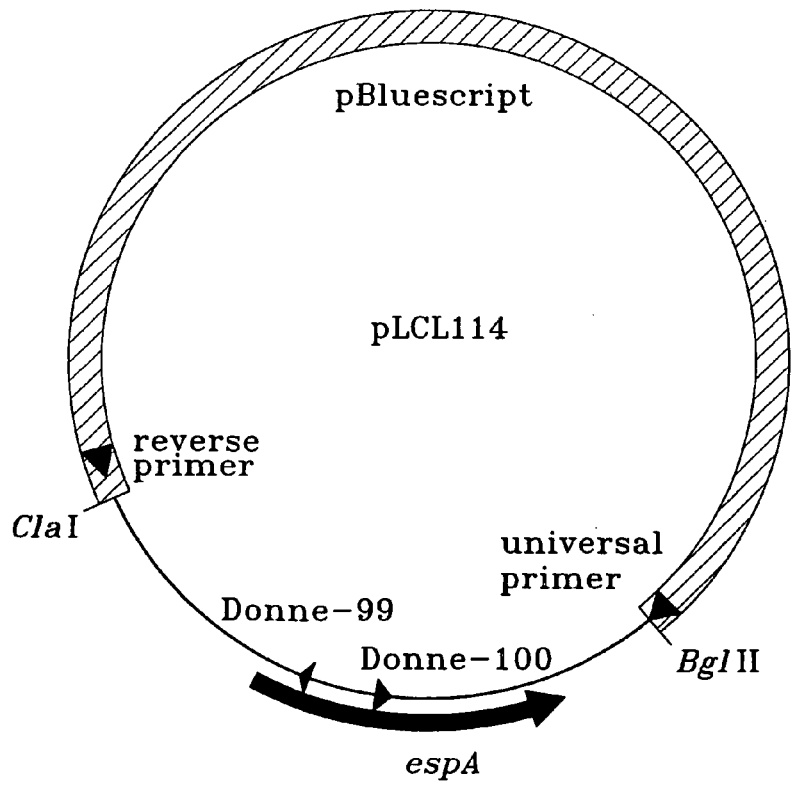

Nucleotide and amino acid sequences have been deposited into the EMBL GenBank and their accession numbers are as follows: RDEC-1 espA (U80908), RDEC-1 espB (U80796), enteropathogenic *Escherichia coli* strain E2348/69 espA (Z54352), enteropathogenic *Escherichia coli* strain E2348/69 espB (Z21555), enteropathogenic *Escherichia coli* strain 69 espD (Y09228), enterohemorrhagic *Escherichia coli* strain EDL933 serotype 0157 espB (X96953), enterohemorrhagic *Escherichia coli* strain 413/89-1 serotype 026 espB (X99670).

DETAILED DESCRIPTION OF ILLUSTRATIVE EMBODIMENTS

The present invention provides a polypeptide, called EspA, which is secreted by pathogenic *E. coli*, such as the enteropathogenic (EPEC) and enterohemorrhagic (EHEC) *E. coli*. Diagnosis of disease caused by such pathogenic *E. coli* can be performed by standard techniques, such as those based upon the use of antibodies which bind to EspA to detect the protein, as well as those based on the use of nucleic acid probes for detection of nucleic acids encoding EspA polypeptide. The invention also provides isolated nucleic acid sequences encoding EspA polypeptide, EspA peptides, a recombinant method for producing recombinant EspA, antibodies which bind to EspA, and a kit for the detection of EspA-producing *E. coli*. The invention also provides a method of immunizing a host with EspA to induce a protective immune response to EspA.

The details of the preferred embodiments of the present invention are set forth in the accompanying drawings and the description below.

As used herein, the term "EspA" (for EPEC secreted [or signaling] protein A) refers to a polypeptide which is a secreted protein from enteropathogenic or enterohemorrhagic *E. coli* and has a molecular weight of about 25 kilodaltons as determined by SDS-PAGE. EspA is an enteropathogenic *E. coli*-secreted protein necessary for activating epithelial cell signal transduction, intimate contact, and formation of attaching and effacing lesions, processes correlated with disease. An example of epithelial cells are cells.

As used herein, the term "polypeptide" encompasses any naturally occurring allelic variant thereof as well as manufactured recombinant forms. As used herein, EspA polypeptides encompass both naturally occurring and recombinant forms, i.e., non naturally occurring forms of the protein and the peptide that are sufficiently identical to naturally occurring EspA peptide to have a similar function of causing pathogenicity. Examples of such polypeptides include the EspA polypeptides from enteropathogenic and enterohemorrhagic *E. coli*, but are not limited to them. Protein and polypeptides include derivatives, analogs and peptidomimetics. Alternatively, EspA peptides can be chemically synthesized using synthesis procedures known to one skilled in the art. Preferably, an automated peptide synthesizer is used with N$^{\alpha}$Fmoc amino acids on a polyethylene glycolpolystyrene (PEGPS) graft resin. Suitable linkers such as a peptide amide linker (PAL) can be used, for example, to create carboxamide end groups.

The term "substantially pure" is used herein to describe a molecule, such as a polypeptide (e.g., an EspA polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify EspA polypeptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

EspA polypeptides included in the invention can have one of the amino acid sequences of EspAs from human or rabbit enteropathogenic *E. coli*, for example, the amino acid sequence of FIG. 1 or FIGS. 4A–D. EspA polypeptides, such as those shown in FIGS. 1 and 4A–D, can be characterized by being approximately 25 kD as determined by SDS-PAGE.

Also included in the invention are polypeptides having sequences that are "substantially identical" to the sequence of an EspA polypeptide, such as one of EspAs in FIGS. 1 and 4A–D. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine), or by one or more nonconservative substitutions, deletions, or insertions, provided that the polypeptide retains at least one EspA-specific activity or an EspA-specific epitope. For example, one or more amino acids can be deleted from an EspA polypeptide, resulting in modification of the structure of the polypeptide, without significantly altering its biological activity. For example, amino- or carboxyl-terminal amino acids that are not required for EspA biological activity, can be removed. Such modifications can result in the development of smaller active EspA polypeptides.

Other EspA polypeptides included in the invention are polypeptides having amino acid sequences that are at least 50% identical to the amino acid sequence of an EspA polypeptide, such as any of EspAs in FIGS. 1 and 4A–D. The length of comparison in determining amino acid sequence homology can be, for example, at least 15 amino acids, for example, at least 20, 25, or 35 amino acids. Homology can be measured using standard sequence analysis software (e.g., Sequence Analysis Software Package of the Genetics Computer Group, University of Wisconsin Biotechnology Center, 1710 University Avenue, Madison, Wis. 53705; also see *Current Protocols in Molecular Biology*, Ausubel, et al., ed., 1989).

The invention also includes fragments of EspA polypeptides that retain at least one EspA-specific activity or epitope. For example, an EspA polypeptide fragment containing, e.g., at least 8–10 amino acids can be used as an immunogen in the production of EspA-specific antibodies. The fragment can contain, for example, an amino acid sequence that is conserved in EspAs. In addition to their use as peptide immunogens, the above-described EspA fragments can be used in immunoassays, such as ELISAs, to detect the presence of EspA-specific antibodies in samples.

The EspA polypeptides of the invention can be obtained using any of several standard methods. For example, EspA polypeptides can be produced in a standard recombinant expression system (see below), chemically synthesized (this approach may be limited to small EspA peptide fragments), or purified from tissues in which they are naturally expressed (see, e.g., Ausubel, et al., supra).

The invention also provides isolated nucleic acid molecules that encode the EspA polypeptides described above, as well as fragments thereof. For example, nucleic acids that encode EspAs as in FIGS. 1 and 4A–D are included in the invention. These nucleic acids can contain naturally occurring nucleotide sequences (see FIGS. 1 and 4A D), or sequences that differ from those of the naturally occurring nucleic acids that encode EspAs, but encode the same amino acids, due to the degeneracy of the genetic code. The nucleic acids of the invention can contain DNA or RNA nucleotides, or combinations or modifications thereof.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of EspA gene products (e.g., EspA RNAs and EspA polypeptides; see below). In addition, the nucleic acid molecules that encode EspA polypeptides (and fragments thereof) and related nucleic acids, such as (1) nucleic acids containing sequences that are complementary to, or that hybridize to, nucleic acids encoding EspA polypeptides, or fragments thereof (e.g., fragments containing at least 12, 15, 20, or 25 nucleotides); and (2) nucleic acids containing sequences that hybridize to sequences that are complementary to nucleic acids encoding EspA polypeptides, or fragments thereof (e.g., fragments containing at least 12, 15, 20, or 25 nucleotides); can be used in methods focused on their hybridization properties. For example, as is described in further detail below, such nucleic acid molecules can be used in the following methods: PCR methods for synthesizing EspA nucleic acids, methods for detecting the presence of an EspA nucleic acid in a sample, screening methods for identifying nucleic acids encoding new EspA family members, and therapeutic methods.

The invention also includes methods for identifying nucleic acid molecules that encode members of the EspA polypeptide family in addition to EspAs shown in FIGS. 1 and 4A–D. In these methods, a sample, e.g., a nucleic acid library, such as a cDNA library, that contains a nucleic acid encoding an EspA polypeptide is screened with an EspA-specific probe, e.g., an EspA-specific nucleic acid probe. EspA-specific nucleic acid probes are nucleic acid molecules (e.g., molecules containing DNA or RNA nucleotides, or combinations or modifications thereof) that specifically hybridize to nucleic acids encoding EspA polypeptides, or to complementary sequences thereof. The term "EspA-specific probe;" in the context of this method of invention, refers to probes that bind to nucleic acids encoding EspA polypeptides, or to complementary sequences thereof, to a detectably greater extent than to nucleic acids encoding other polypeptides, or to complementary sequences thereof. The term "EspA-specific probe" thus includes probes that can bind to nucleic acids encoding EspA polypeptides (or to complementary sequences thereof).

The invention facilitates production of EspA-specific nucleic acid probes. Methods for obtaining such probes can be designed based on the amino acid sequence alignments shown in FIGS. 1–3B. The probes, which can contain at least 12, e.g., at least 15, 25, 35, 50, 100, or 150 nucleotides, can be produced using any of several standard methods (see, e.g., Ausubel, et al., supra). For example, preferably, the probes are generated using PCR amplification methods. In these methods, primers are designed that correspond to EspA-conserved sequences, which can include EspA-specific amino acids, and the resulting PCR product is used as a probe to screen a nucleic acid library, such as a cDNA library. A nucleotide sequence encoding EspA was identified generally following this process based upon the analysis of the sequences of EspA in FIGS. 1 and 4A–D.

As is known in the art, PCR primers are typically designed to contain at least 15 nucleotides, for example 15–30 nucleotides. The design of EspA-specific primers containing 21 nucleotides, which encode EspA peptides containing 7 amino acids, are described as follows. Preferably, most or all of the nucleotides in such a probe encode EspA-conserved amino acids, including EspA-specific amino acids. For example, primers containing sequences encoding peptides containing at least 40% EspA-conserved amino acids can be used. Such a primer, containing 21 nucleotides, can include sequences encoding at least 3 EspA-conserved amino acids. Thus, the primer can contain sequences encoding at least one EspA-specific amino acid, for example, up to 7 EspA-specific amino acids. Once EspA-specific amino acid sequences are selected as templates against which primer sequences are to be designed, the primers can be synthesized using, e.g., standard chemical methods. As is described above, due to the degeneracy of the genetic code, such primers should be designed to include appropriate degenerate sequences, as can readily be determined by one skilled in the art.

As used herein, the term "espA" refers to polynucleotide encoding the EspA polypeptide. These polynucleotides include DNA, cDNA and RNA sequences which encode EspA. All polynucleotides encoding all or a portion of EspA are also included herein. Such polynucleotides include naturally occurring, synthetic, and intentionally manipulated polynucleotides. For example, a espA polynucleotide can be subjected to site-directed mutagenesis. The espA polynucleotide sequence also includes antisense sequences. All degenerate nucleotide sequences are included in the invention as long as the amino acid sequence of EspA peptide encoded by the nucleotide sequence is functionally unchanged.

This invention encompasses nucleic acid molecules that hybridize to the polynucleotide of the invention. As used herein, the term "nucleic acid" encompasses RNA as well as single and double-stranded DNA and cDNA. The polynucleotide encoding EspA includes the nucleotide sequence in FIGS. 1 and 4A–D, as well as nucleic acidsequences complementary to that sequence. A complementary sequence may include an antisense nucleotide. When the sequence is RNA, the deoxynucleotides A, Q C, and T of FIGS. 1 and 4A–D are replaced by ribonucleotides A, Q C, and U, respectively. Also included in the invention are fragments of the above-described nucleic acid sequences that are at least 15 bases in length, which is sufficient to permit the fragment to selectively hybridize to DNA that encodes the protein of FIG. 1 or 4A–D under physiological conditions.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences of the invention can be obtained by several methods. For example, the DNA can be isolated using hybridization techniques which are well known in the art. These include; but are not limited to (1) hybridization of libraries with probes to detect homologous nucleotide sequences, (2) polymerase chain reaction (PCR) on DNA using primers capable of annealing to the DNA sequence of interest, and (3) antibody screening of expression libraries to detect cloned DNA fragments with shared structural features.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically or produced by fragmentation of the native sequence. Chemical synthesis requires that short, oligopeptide stretches of amino acid sequence be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. When used in combination with polymerase chain reaction technology, even rare expression products can be cloned.

The invention provides nucleic acid sequences encoding the EspA polypeptides, vectors and host cells containing them and methods of expression. After a peptide of EspA is isolated, nucleic acids encoding the peptide can be isolated by methods well known in the art. These isolated nucleic acids can be ligated into vectors and introduced into suitable host cells for expression. Methods of ligation and expression of nucleic acids within cells are well known in the art (see, Sambrook et al., *Molecular Cloning: A Laboratory Manual*, Cold Spring Harbor Laboratory, Cold Spring Harbor, N.Y., 1989, incorporated herein by reference).

As used herein, the terms "espB" and "eaeA" refer to genes other than espA that encode enteropathogenic *E. coli*-secreted proteins. As used herein, the term "EspB" and "EaeX" refer to the proteins encoded by the espB and the eaeA genes, respectively.

The invention provides vectors containing polynucleotides encoding the EspA polypeptide. For example, the plasmid (pMSD2) with an intact espA can restore secretion of the EspA protein in an espA deficient strain. As used herein, "vectors" includes plasmids, DNA and RNA viral vectors, baculoviral vectors, vectors for use in yeast, and other vectors well known to those of skill in the art. Several types of vectors are commercially available and can be used to practice this invention. Examples of vectors useful in the practice of this invention include those as widely varied as the low-copy vector pMW118, the positive-selection suicide vector pCVD442, and the commercially available pBluescript II SK(+) (Stragene, La Jolla, Calif.).

When the vector is a plasmid, it generally contains a variety of components including promoters, signal sequences, phenotypic selection genes, origins of replication sites, and other necessary components as are known to those of skill in the art. Promoters most commonly used in prokaryotic vectors include the lacZ promoter system, the alkaline phosphatase pho A promoter, the bacteriophage λPL promoter (a temperature sensitive promotor), the tac promoter (a hybrid trp-lac promoter regulated by the lac repressor), the tryptophan promoter, and the bacteriophage T7 promoter. For example, the low-copy vector pMW118 under control of the lacZ promoter.

A signal sequence is typically found immediately 5' to the nucleic acid encoding the peptide, and will thus be transcribed at the amino terminus of the fusion protein.

Typical phenotypic selection genes are those encoding proteins that confer antibiotic resistance upon the host cell. For example, ampicillin resistance gene (amp) and the tetracycline resistance gene (tet) are readily employed for this purpose. For a different example, the aphA-3 cassette, encoding a gene for resistance to kanamycin (kan), may be cloned into the region of vector containing polynucleotides encoding the EspA polypeptide for selection of the vector on kanamycin plates.

Construction of suitable vectors containing polynucleotides encoding EspA polypeptide are prepared using standard recombinant DNA procedures well known to those of skill in the art. Isolated polynucleotides encoding the EspA polypeptide to be combined to form the vector are cleaved and ligated together in a specific order and orientation to generate the desired vector.

The invention provides a host cell containing a vector having a polynucleotide encoding the EspA polypeptide. The polynucleotides of the present invention can be used to produce transformed or transfected cells for enhanced production of the expressed EspA. EspA can be isolated from transformed cells by standard methods well known to those of skill in the art. The protein could be isolated, for example, using immunoaffinity purification.

DNA sequences encoding EspA can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the EspA polynucleotide sequences may be inserted into a recombinant expression vector. The term "recombinant expression vector" refers to a plasmid, virus or other vehicle known in the art that has been manipulated by insertion or incorporation of the EspA genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells.

Polynucleotide sequences encoding EspA can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired. For another example, triparental conjugation may be used to genetically introduce vector into *E. coli*, especially enteropathogenic *E. coli* or rabbit enteropathogenic *E. coli*. The transformed cells are selected by growth on an antibiotic, commonly tetracycline (tet) or ampicillin (amp), to which they are rendered resistant due to the presence of tet or amp resistance genes on the vector. In a specific embodiment, cells are selected on the basis of resistance to kanamycin and sucrose.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the EspA of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal orpolyclonal antibodies.

Among the prokaryotic organisms which may serve as host cells are *E. coli* strain JM101, *E. coli* K12 strain 294 (ATCC number 31,446), *E. coli* strain W3110 (ATCC number 27,325), *E. coli*X1776 (ATCC number 31,537), *E. coli* XL-1Blue (Stratagene), and *E. coli* B; however, many other strains of *E. coli*, such as HB101, NM522, NTM538, NM539 and many other species and genera of prokaryotes can be used as well. Besides the *E. coli* strains listed above, bacilli such as *Bacillus subtillis*, other enterobacteriaceae such as *Salmonella typhimunium* or *Serratia marcesans* and various *Pseudomonas* species can all be used as hosts. In one specific embodiment, the prokaryotic host cell is enteropathogenic *E. coli*. In another specific embodiment, the prokaryotic host cell is rabbit enteropathogenic *E. coli*.

Among the eukaryotic organisms which may serve as host cells are yeast strains such as PS23-6A, W301-18A, LL20, D234-3, INVSC1, INVSC2, YJJ337. Promoter and enhancer sequences such as gal 1 and pEFT-I are useful. Vra-4 also provides a suitable enhancer sequence. Sequences useful as functional origins of replication include ars1 and 2μ circular plasmid.

The Gram-negative bacteria are a diverse group of organisms and include Spirochaetes such as *Treponema* and *Borrelia*, Gram-negative bacilli including the Pseudomonadaceae, Legionellaceae, Enterobacteriaceae, Vibrionaceae, Pasteurellaceae, Gram-negative cocci such as Neisseriaceae, anaerobic Bacteroides, and other Gram-negative bacteria including *Rickettsia, Chlamydia,* and *Mycoplasma.*

Gram-negative bacilli (rods) are important in clinical medicine. They include (1) the Enterobacteriaceae, a family which comprises many important pathogenic genera, (2) *Vibrio, Campylobacter* and *Helicobacter* genera, (3) opportunistic organisms (e.g., *Pseudomonas, Flavobacterium,* and others) and (4) *Haemophilus* and *Bordetella* genera. The Gram-negative bacilli are the principal organisms found in infections of the abdominal viscera, peritoneum, and urinary tract, as well secondary invaders of the respiratory tracts, burned or traumatized skin, and sites of decreased host resistance. Currently, they are the most frequent cause of life-threatening bacteremia. Examples of pathogenic Gram-negative bacilli are E. toll (diarrhea, urinary tract infection, meningitis in the newborn), *Shigella* species (dysentery), *Salmonella typhi* (typhoid fever), *Salmonella typhimurium* (gastroenteritis), *Yersinia enterocolitica* (enterocolitis), *Yersinia pestis* (black plague), *Vibrio cholerae* (cholera), *Campylobacter jejuni* (enterocolitis), *Helicobacter jejuni* (gastritis; peptic ulcer), *Pseudomonas aeruginosa* (opportunistic infections including burns, urinary tract, respiratory tract, wound infections, and primary infections of the skin, eye and ear), *Haemophilus influenzae* (meningitis in children, epiglottitis, otitis media, sinusitis, and bronchitis), and *Bordetella pertussis* (whooping cough). *Vibrio* is a genus of motile, Gram-negative rod-shaped bacteria (family Vibrionaceae). *Vibrio cholerae* causes cholera in humans; other species of *Vibrio* cause animal diseases. *E. coli* colonize the intestines of humans and warm blooded animals, where they are part of the commensal flora, but there are types of *E. coli* that cause human and animal intestinal diseases. They include the enteroaggregative *E. coli* (EaggEC), enterohaemorrhagic *E. coli* (EHEC), enteroinvasive *E. coli* (EIEC), enteropathogenic *E. coli* (EPEC) and enterotoxigenic *E. coli* (ETEC). Uropathogenic *E. coli* (UPEC) cause urinary tract infections. There are also neonatal meningitis *E. coli*(NMEC). Apart from causing similar infections in animals as some of the human ones, there are specific animal diseases including: calf septicaemia, bovine mastitis, porcine oedema disease, and air sac disease in poultry.

The *Neisseria* species include *N. cinerea, gonorrhoeae, N. gonorrhoeae* subsp. *kochii, N. lactamica, N. meningitides, N. polysaccharea, N. mucosa, N. sicca, N. subflava,* the asaccharolytic species *N. flavescens, N. caviae, N. cuniculi* and *N. ovis.* The strains of *Moraxella* (*Branhamella*) *catarrhalis* are also considered by some taxonomists to be *Neisseria.* Other related species include *Kingella, Eikenella, Simonsiella, Alysiella,* CDC group EF-4, and CDC group M-5. *Veillonella* are Gram-negative cocci that are the anaerobic counterpart of *Neisseria.* These non-motile diplococci are part of the normal flora of the mouth.

The pathogenic bacteria in the Gram-negative aerobic cocci group include *Neisseria, Moraxella* (*Branhamella*), and the *Acinetobacter.* The genus *Neisseria* includes two important human pathogens, *Neisseria gonorrhoeae* (urethritis, cervicitis, salpingitis, proctitis, pharyngitis, conjunctivitis, pharyngitis, pelvic inflammatory disease, arthritis, disseminated disease) and *Neisseria meningitides* (meningitis, septicemia, pneumonia, arthritis, urethritis). Other Gram-negative aerobic cocci that were previously considered harmless include *Moraxella* (*Branhamella*) *catarrhalis* (bronchitis and bronchopneumonia in patients with chronic pulmonary disease, sinusitis, otitis media) has recently been shown to be an common cause of human infections.

The EspA polypeptides of the invention can also be used to produce antibodies which are immunoreactive or bind to epitopes of the EspA polypeptides. Antibody which consists essentially of pooled monoclonal antibodies with differentepitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

The term "antibody" as used in this invention includes intact molecules as well as fragments thereof, such as Fab, Fab', F(ab')$_2$, and Fv that can bind the epitope. These antibody fragments retain some ability selectively to bind with its antigen or receptor and are defined as follows:

(1) Fab, the fragment that contains a monovalent antigen-binding fragment of an antibody molecule can be produced by digestion of whole antibody with the enzyme papain to yield an intact light chain and part of one heavy chain;

(2) Fab', the fragment of an antibody molecule can be obtained by treating whole antibody with pepsin, followed by reduction, to yield an intact light chain and part of the heavy chain; two Fab' fragments are obtained per antibody molecule;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody, defined as a genetically engineered molecule containing the variable region of the light chain, the variable region of the heavy chain, linked by a suitable peptide linker as a genetically fused single chain molecule.

Methods of making these fragments are known in the art. (See, for example, Harlow and Lane, *Antibodies: A Laboratory Manual,* Cold Spring Harbor Laboratory, New York (current edition), incorporated herein by reference).

An epitope is any antigenic determinant on an antigen to which the paratope of an antibody binds. Epitopes usually consist of chemically active surface groupings of molecules such as amino acids or sugar side chains and usually have specific three dimensional structural characteristics, as well as specific charge characteristics.

If needed, polyclonal or monoclonal antibodies can be further purified, for example, by binding to and elution from a matrix to which the peptide or a peptide to which the antibodies are raised is bound. Those of skill in the art will know of various techniques common in the immunology arts for purification and/or concentration of polyclonal antibodies, as well as monoclonal antibodies (See, e.g., Coligan, et al., Unit 9, *Current Protocols in Immunology,* Wiley Interscience, current edition, incorporated by reference).

The invention also provides peptide epitopes for use in designing espA specific nucleotide probes or anti-EspA antibodies. Such probes or antibodies can be used to identify proteins or genes that may be involved in the virulence of other pathogens, including but not limited to polypeptides or polynucleotides from Gram-negative bacteria.

The antibodies of the invention, including polyclonal and monoclonal antibodies, chimeric antibodies, single chain antibodies and the like, have with the ability to bind with high immunospecificity to the EspA proteins, peptides or nucleotide sequences of the invention, or fragments thereof. These antibodies can be unlabeled or suitably labeled. Antibodies of the invention can be used for affinity purification of EspA for example. Antibodies of the invention may be employed in known immunological procedures for qualitative or quantitative detection of these proteins or peptides in cells, tissue samples, sample preparations or fluids. Antibodies of the invention may be employed in known immunological procedures for qualitative or quantitative detection of the nucleotide sequences or portions thereof.

The invention provides a method for detecting EspA polypeptide in a sample, including contacting a sample from a subject with an antibody to EspA polypeptide; and detecting binding of the antibody to EspA polypeptide. Binding is indicative of the presence of EspA polypeptide in the sample. As used herein, the term "sample" includes material derived from a mammalian or human subject or other animal. Such samples include but are not limited to hair, skin samples, tissue sample, cultured cells, cultured cell media, and biological fluids. For example, EspA polypeptide can be detected in HeLa cell (e.g., human) culture.

As used herein, the term "tissue" refers to a mass of connected cells (e.g., CNS tissue, neural tissue, or eye tissue) derived from a human or other animal and includes the connecting material and the liquid material in association with the cells. For example, rabbit enteropathogenic E. coli can be found in the stomach, cecum and colon of rabbits. As used herein, the term "biological fluid" refers to liquid material derived from a human or other animal. Such biological fluids include but are not limited to blood, plasma, serum, serum derivatives, bile, phlegm, saliva, sweat, amniotic fluid, and cerebrospinal fluid (CSF), such as lumbar or ventricular CSF.

As used herein, the term "sample" also includes solutions containing the isolated polypeptide, media into which the polypeptide has been secreted, and media containing host cells which produce the EspA polypeptide. For example, a sample may be a protein samples which is to be resolved by SDS-PAGE and transferred to nitrocellulose for Western immunoblot analysis. The quantity of sample required to obtain a reaction may be determined by one skilled in the art by standard laboratory techniques. The optimal quantity of sample may be determined by serial dilution.

In one embodiment, the presence of EspA polypeptide in the sample is indicative of infection by enteropathogenic E. coli. In another embodiment, the presence of EspA polypeptide in the sample is indicative of infection by enterohemonhagic E. coli.

Proteins, protein fragments, and synthetic peptides of the invention are projected to have numerous uses including prognostic, therapeutic, diagnostic or drug design applications. Proteins, protein fragments, and synthetic peptides of the invention will provide the basis for preparation of monoclonal and polyclonal antibodies specifically immunoreactive with the proteins of the invention. In one embodiment, the invention provides a method of immunizing a host susceptible to disease caused by EspA-producing E. coli, by administering to a host with the polypeptide of claim 1; and inducing a protective immune response in the host to EspA polypeptide. The infection of the host by EspA-producing organism is thereby prevented. In a more specific embodiment, the EspA-producing organism is an E. coli strain. In a more specific embodiment, the E. coli strain is either enteropathogenic or enterohemorrhagic E. coli.

In another embodiment, the invention provides a method of ameliorating disease caused by EspA-producing organism, by immunizing a host with EspA polypeptide and inducing an immune response in the host to the EspA polypeptide. In a more specific embodiment, the EspA-producing organism is an E. coli strain. In an even more specific embodiment, the E. coli strain is either enteropathogenic or enterohemonrhagic E. coli. The invention provides a method for detecting espA polynucleotide in a sample, by contacting a sample suspected of containing espA polynucleotide with a nucleic acid probe that hybridizes to espA polynucleotide; and detecting hybridization of the probe with espA polynucleotide. The detection of hybridization is indicative of espA polynucleotide in the sample.

In another embodiment, the invention provides an organism with a mutated espA gene. Preferred organisms in which an espA gene may be mutated include but are not limited to bacteria. Among the bacteria in which an espA gene may be mutated are E. coli. Among the E. coli in which an espA gene may be mutated are enteropathogenic and-enterohemorrhagic E. coli.

The invention provides a recombinant method for producing espA polynucleotide, including inserting a nucleic acid encoding a selectable marker into the polynucleotide encoding EspA polypeptide. The resulting polynucleotide encodes a recombinant EspA polypeptide containing the selectable marker. For example, a selectable marker may be a herpes simplex virus (HSV) tag, for which there are commercially available antibodies.

The invention provides a recombinant method for producing EspA polypeptide, by growing a host cell containing a polynucleotide encoding EspA polypeptide under conditions which allow expression and secretion of EspA polypeptide; and isolating the polypeptide. Methods of producing polypeptides and peptides recombinantly are within the scope of this invention. As used herein, the term "conditions which allow expression and secretion" refers to suitable conditions such that the nucleic acid is transcribed and translated and isolating the polypeptide so produced. The polypeptide produced may be a protein secreted into the media. Media includes a fluid, substance or organism where microbial growth can occur or where microbes can exist. Such environments can be, for example, animal tissue or bodily fluids, water and other liquids, food, food products or food extracts, and certain inanimate objects. For example, microbes may grow in Luria-Bertani (LB) media. It is not necessary that the environment promote the growth of the microbe, only that it permits its subsistence.

The invention provides a method to identify a compound which inhibits bacterial type III secretion systems, by introducing the polynucleotide encoding a selectable marker into bacteria having a bacterial type II secretion system; growing the bacteria under conditions which allow growth of bacteria and secretion of the polypeptide encoded by the polynucleotide; contacting a compound suspected of inhibiting the bacterial type III secretion system with the bacteria; inducing the expression of the polypeptide; and detecting the secretion of the polypeptide. In the practice of the method, a lack of secretion is indicative of the inhibition of bacterial type III secretion systems. As used in this invention, the term "type III secretion" and "type III secretion" pathway refer to a specialized machinery to export molecules across a cell membrane. Exporting molecules across a cell membrane is a process critical for moving virulence factors to the surface where they can interact with host cell components. The type III secretion pathway uses adenosine triphosphate (ATP) as an energy source. The type III secretion pathway is different than other secretion pathways found in Gram-negative bacteria, although it is homologous to flagella and filamentous phage assembly genes. It does not resemble any mammalian pathway. It is always associated with disease production. The virulence factors secreted by the type II secretion pathway vary between pathogens, although components of the type III secretion machinery are interchangeable, at least for *Salmonella, Shigella*, and *Yersinia*.

Furthermore, the polypeptide or nucleotide sequences of the invention can be used to identify compounds or compositions which interact (e.g., bind) with them and affect their biological activity. Such effects include inhibition or stimulation of EspA activity or secretion.

The invention provides a method for producing a non-pathogenic organism, by generating a mutation in a polynucleotide encoding EspA polypeptide; inserting a nucleic acid sequence encoding a selectable marker into the site of the mutation; introducing the mutated espA polynucleotide into a chromosomal espA gene of an organism to produce a mutation in the chromosomal espA gene; and selecting organisms having the mutation. As used herein, the term "mutation" refers to a change in the nucleotide sequence of a gene, in particular, the polynucleotide encoding EspA polypeptide. Mutations include mutations producing EspA polypeptide with a different amino acid sequence, missense mutations (including frame shift mutations), nonsense mutations (including knockout mutations), and recombinant genetic techniques which produce fusion proteins containing part of the EspA polypeptide. In one embodiment, the nucleic acid sequence encoding a selectable marker encodes resistance to kanamycin. For example, the aphA-3 cassette, encoding a gene for resistance to kanamycin (kan), may be cloned into the polynucleotides encoding the EspA polypeptide for selection of the mutated espA polynucleotide on kanamycin plates to produce a knockout mutation.

Preferred organisms in which to practice the invention include but are not limited to bacteria. In another embodiment, the organism which is used to generate a mutation in a polynucleotide encoding EspA polypeptide is *E. coli*. Among the *E. coli* that may be transformed are enteropathogenic and enterohemorrhagic *E. coli*.

The invention provides a method of activating tyrosine kinase activity in a host cell by adding both mutant espA-deficient organisms that express Eae polypeptide and mutant eaeA-deficient organisms that express EspA polypeptide to a host cell and binding the bacteria to the host cell; thereby activating host cell tyrosine kinase activity in the cell. In one embodiment, the activation of host cell tyrosine kinase activity in the cell causes the tyrosine phosphorylation of a 90 kilodalton host membrane protein, Hp90, and fluxes of intracellular inositol phosphate ($IP_3$) and calcium. For example, an eaeA mutant can be used to complement an espA mutant for invasion when these two mutant strains were used to co-infect HeLa cells. The invention thus provides a useful scientific method to investigate pathogenesis by cell biology.

This invention includes a kit containing one or more antibodies of the invention as well as a nucleotide based kit. In one embodiment, the kit is useful for the detection of EspA polypeptide and is a carrier means compartmentalized to receive in close confinement a container containing an antibody which binds to EspA polypeptide. As used herein, a "container means" includes vials, tubes, and the like, each of the container means comprising one of the separate elements to be used in the method. In one embodiment, the antibody which binds to EspA polypeptide is detectably labeled. In a more specific embodiment, the label is selected from the group consisting of radioisotope, a bioluminescent compound, a chemiluminescent compound, a fluorescent compound, a metal chelate, and an enzyme.

In another embodiment, the kit is useful for the detection of an espA polynucleotide and is a carrier means compartmentalized to receive in close confinement a container containing the nucleic acid probe that hybridizes to espA polynucleotide. In one embodiment, nucleic acid probe that hybridizes to espA polynucleotide is detectably labeled. In a more specific embodiment, the label is selected from the group consisting of radioisotope, a bioluminescent compound, a chemiluminescent compound, a fluorescent compound, a metal chelate, and an enzyme.

Since EspA is a secreted protein, it is useful as a fusion partner for cloning and expressing other peptides and proteins. For example, EspA fused to a protein of interest is recombinantly produced in a host cell, e.g., *E. coli*, and the fusion protein is secreted into the culture media in which the transformed host is grown. The fusion protein can be isolated by anti-EspA antibodies followed by cleavage of EspA from the peptide or protein of interest. ELISA or other immunoaffinity methods can be used to identify the EspA fusion protein. The invention provides a method of producing an EspA fusion protein including growing a host cell containing a polynucleotide encoding EspA operably linked to a polynucleotide encoding a polypeptide or peptide of interest under conditions which allow expression and secretion of the fusion polypeptides and isolating the fusion polypeptide. The term "operably linked or associated" refers to functional linkage between a promoter sequence and the structural gene or genes in the case of a fusion protein, regulated by the promoter nucleic acid sequence. The operably linked promoter controls the expression of the polypeptide encoded by the structural gene (e.g., the fusion protein).

The following examples are intended to illustrate but not limit the invention. While they are typical of those that might be used, other procedures known to those skilled in the art may alternatively be utilized.

EXAMPLE 1

DNA Sequence Analysis of the Enteropathogenic *E. coli* espA Gene

The purpose of this Example is to characterize espA, a gene responsible for the attaching and effacing activity of enteropathogenic *E. coli*. The espA gene encodes the 25 kilodalton secreted protein and is located on the enteropathogenic *E. coli* genome in the Locus of Enterocyte Effacement between eaeA and espB, two loci required for intimate adherence.

The DNA sequence of the enteropathogenic *E. coli* Locus of Enterocyte Effacement between eaeA and espB was determined. DNA sequencing was performed as follows: The SalI-BglII DNA fragment of the Locus of Enterocyte Effacement spanning from within eaeA to upstream (5') of espB was cloned into the commercially available plasmid pBluescript to create the plasmid pLCL109. A series of nested DNA deletions was made from the end of the plasmid pLCL109 closer to the eaeB gene. These DNA deletions of plasmid pLCL109 were used as templates to determine the nucleotide sequence of both strands of DNA using oligonucleotide primers synthesized as needed, [a-$^{35}$S]dATP, and the Sequenase enzyme. DNA sequence data were analyzed with the package developed by the Genetics Computer Group of the University of Wisconsin.

Analysis of the DNA sequence showed three open reading frames. The amino acid sequence predicted by the DNA sequence at the 5' end of the second open reading frame (espA) was identical to the amino-terminal sequence of a protein with an $M_R$ of approximately 25 kalton secreted by enteropathogenic E. coli. No proteins with similar sequences were detected in a search of the Genbank database using the TFASTA. Therefore the espA gene encodes the secreted enteropathogenic E. coli protein.

The predicted molecular weight of the entire protein encoded by espA is 20,468 daltons (FIG. 1). No leader sequence precedes the amino-terminus of the reported secreted product. A strong consensus ribosome binding site ends seven nucleotides prior to the start codon. Eleven of the first nineteen residues at the amino-terminus were predicted to be serine or threonine.

EXAMPLE 2

Construction of a Mutation is an espA Gene on a Plasmid and on a Chromosome

The purpose of this Example was to construct a mutation in an espA gene on the chromosome of an organism. The purpose of this Example was to construct a mutation in an espA gene on a plasmid. The plasmid can then be used to create mutations in the espA gene of other organisms. Plasmids with a nonpolar mutation in espA gene were constructed. Furthermore, a mutant bacterial strain with a nonpolar mutation in its chromosomal espA gene was generated.

An espA gene with a nonpolar mutation is described in FIGS. 2A–D. The use of the polymerase chain reaction (PCR) generated a deletion with restriction sites that allow an aphA-3 cassette, encoding resistance to kanamycin, to be cloned into the deleted region. This aphA-3 cassette is preceded (5') by translation stop codons in all three reading frames and immediately followed (3') by a consensus ribosome binding site and a start codon. The insertion into the espA gene was engineered to retain the reading frame of the 3' end of espA and to therefore allow unaffected transcription and translation of downstream 3' genes. DNA sequencing confirmed the reading frame of the mutation.

The construction of a nonpolar mutation in the espA gene on a plasmid was performed by the polymerase chain reaction as follows: The PCR template was plasmid pLCL114, containing the ClaI-BhIII fragment of pLCL109 cloned into pBluescript. Two pairs of primers were used, the universal primer with Donne-99 and the reverse primer with Donne-100: Oligonucleotides Donne-99 and Donne-100 are nucleotides 4157 through 4140 and 4297 through 4324 of the Sall-BgIII fragment, respectively. For cloning purposes, an NruI restriction site was engineered into the 5' end of both Donne-99 and Donne-100. Oligonucleotides were constructed at the Biopolymer Laboratory of the University of Maryland at Baltimore. PCR was performed on 50 µL samples in a minicyler. The PCR reaction was thirty cycles of DNA denaturation at 94° C. for one minute, annealing to the primers at 55° C. for two minutes, and polynucleotide extension at 72° C. for three minutes. The two resulting amplified fragments amplified were each cloned into the commercially available plasmid pCRscript to create pLC1119 and pLCL120, respectively. The insert of pLCL120 was then cloned into pLCL119 using Sall and NruI to create pLCL121 containing the desired deletion. The 850 base pair aphA-3 kanamycin resistance cassette flanked by SmaI sites was then inserted into the NruI site of pLCL121.

The mutated espA allele was cloned in the positive-selection suicide vector pCVD442 and introduced into wild-type enteropathogenic E. coli strain E2348/69 by allelic exchange. A espA mutant bacterial strain was constructed as follows: The Sall-SacI fragment from the plasmid with the aphA-3 kanamycin resistance which contained the interrupted espA gene was cloned into positive-selection suicide vector pCVD442 in DHSapir for introduction into E2348/69 by triparental conjugation or by electroporation in 0.1 cm cuvettes with an E. coli pulser set at 1.8 kV.

An espA mutant was selected on modified LB kanamycin plates. The resulting enteropathogenic E. coli mutant strain, UMD872, was resistant to sucrose and kanamycin, and sensitive to ampicillin. PCR amplification using the two primers flanking the mutation, Donne-52 and Donne-73, confirmed the construction of the espA mutation. Bacteria were stored at −70° C. in 50% LB broth/50% glycerol (vol/vol) and grown on LB agar plates or LB broth with chloramphenicol (20 µg/ml), ampicillin (200 µg/ml), nalidixic acid (50 µg/ml), or kanamycin (50 µg/ml) added as needed.

EXAMPLE 3

Disruption of the Enteropathogenic E. coli espA Gene Abolishes Secretion of the EspA Protein The purpose of this Example was to identify the protein encoded by the espA gene. A comparison of the amino-terminal sequence data of the EspA protein agreed with the translated espA gene sequence. To confirm this result, the espA deletion mutant, UMD872, was grown in radiolabeled tissue culture media. The deletion of the espA gene results in the loss of the 25 kilodalton radiolabeled secreted protein. This result was confirmed by immunoprecipitation using an anti-EPEC antisera which reacts with the secreted EspA protein. Western analysis using anti-EPEC antisera showed no 25 kilodalton secreted protein. Secretion of the EspA protein was restored when the espA deficient strain was transformed a plasmid (pMSD2) with an intact espA. The increased production by the bacteria of EspA protein encoded by the plasmid reduced the secretion of the other proteins by the type III secretion pathway.

EXAMPLE 4

Enteropathogenic E. Coli EspA is Required for Invasion of Cultured Epithelial Cells The purpose of this Example was to examine whether the enteropathogenic E. coli EspA protein is involved in epithelial cell invasion. EspA protein is needed for triggering the host signal transduction pathway and invasion of host cells.

Monolayers of an epithelial cancer cell (HeLa) were infected for three hours with either parental wild-type or espA mutant enteropathogenic E. coli strains. The number of adherent and intracellular (i.e., invasive) enteropathogenic E. coli was determined. The absolute number of bacteria adherent to HeLa cells varied between strains, according to the different growth rates between the mutant and parental enteropathogenic E. coli strains. While the espA mutant strain UMD872 adheres efficiently to epithelial cells, it is deficient for invasion. However, UMD872 invaded HeLa monolayers at near wild-type levels when the espA gene was genetically complemented by the plasmid pMSD2, which encodes an intact espA gene.

Co-infection experiments of HeLa monclayers were carried out to determine whether the invasion defective behavior of bacterial strains with mutations in either espA, espB, and eaeA could genetically complement each other in trans to mediate subsequent invasion. The eaeA bacterial mutant strain activates signaling but lacks intimate adherence. Signaling mediated by an eaeA mutant strain allows an espB deficient strain to enter epithelial cells, but not the converse. The eaeA mutant complemented an espA mutant for invasion when these two mutant strains are used to co-infect HeLa cells, but there was no increase in invasion of the eaeA mutant strain. Indeed, the signaling induced by the more adherent eaeA mutant lead to the increased uptake of the espA mutant. Co-infection with espA and espB deleted strains did not enhance invasion of either strain, showing that espA and espB do not complement each other.

Co-infection experiments demonstrated that like espB, the espA mutant behavior was complemented by eaeA but not the reverse. Indeed, the signaling generated by the more adherent eaeA mutant lead to the increased uptake of the intimin expressing espA mutant. In contrast, neither the espA nor the espB mutant strain could complement each other, implying that both proteins may act together at the same step to induce epithelial signaling.

EXAMPLE 5

EspA is Essential to Induce Signal Transduction Events in Epithelial Cells

The purpose of this Example was to determine whether EspA is essential to induce signal transduction events in epithelial cells. Enteropathogenic *E. coli* induce tyrosine phosphorylation of a host cell 90 kilodalton membrane protein and subsequent accumulation of phosphorylated proteins, actin, and other cytoskeletal components beneath adherent bacteria. The ability of an espA mutant defective for invasion to induce these two signaling events in mammalian cells was examined. Unlike wild-type enteropathogenic *E. coli*, the espA mutant strain UMD872 was unable to induce phosphorylation of host Hp90. The ability to induce this phosphorylation event was restored by a plasmid (pMSD2) that encodes the EspA protein.

The adherence and invasion assays were performed as follows: $10^5$ HeLa cells grown in DMEM were infected with the various enteropathogenic *E. coli* strains (m.o.i. 1:100) for three hours. HeLa cells were grown at 37° C. with 5% $CO_2$ in Dulbecco's Minimal Eagles Medium (DMEM) supplemented with 10% (vol/vol) fetal calf serum. Monolayers were washed thrice in phosphate-buffered saline before lysing in 1% Triton (vol/vol) in phosphate-buffered saline and plating out serial dilution on LB agar plates. For invasion assays the washed monolayers were incubated with gentamicin (100 μg/ml) for one hour to kill external bacteria before washing, lysing and plating out.

HeLa cell monolayers were infected for three hours with wild-type or mutant enteropathogenic *E. coli* strains. The epithelial Triton X-100 soluble and insoluble proteins of HeLa cells were isolated. Protein samples were resolved by SDS-PAGE and transferred to nitrocellulose prior to probing with anti-phosphotyrosine specific antibodies.

The isolation of enteropathogenic *E. coli*-secreted proteins and HeLa cellular proteins was accomplished as follows: Tissue culture plates were seeded overnight with $10^6$ HeLa cells. Before infection, the media was replaced with DMEM minus methionine/cysteine containing cycloheximide (100 μg/ml). HeLa cells were grown at 37° C. with 5% $CO_2$ in DMEM supplemented with 10% (vol/vol) fetal calf serum. Enteropathogenic *E. coli* was added (m.o.i. 100:1) and incubated for 2.5 hours at 37° C. in 5% $CO_2$ incubator before adding 200 μg/$^{m'35}$S cysteine/methionine for 30 minutes. The culture supernatant was removed and the bacteria pelleted by centrifugation (18,000×g, 10 minutes). The supernatant secreted proteins were precipitated by the addition of ice cold trichloroacetic acid (10% vol/vol) and incubated on ice for 60 minutes. Proteins were pelleted by centrifugation as above and resuspended in Laemelli sample buffer. Samples were resolved by 12% SDS-PAGE and protein profiles examined by autoradiography or transferred to nitrocellulose prior to probing with anti-EPEC antibodies.

All enteropathogenic *E. coli* strains exhibited a tyrosine phosphorylated 85 kilodalton protein Ep85 in the insoluble fraction, confirming the presence of the enteropathogenic *E. coli* strains on the monolayer.

HeLa phosphotyrosine proteins were analyzed as follows: Infected HeLa monolayers were washed thrice with ice cold phosphate-buffered saline prior to lysis in 1% Triton X-100 in the presence of protease inhibitors. The Triton insoluble and soluble fraction were isolated, resuspended in Laemelli sample buffer, and analyzed for the presence of phosphotyrosine proteins by Western immunoblot analysis with anti-phosphotyrosine antibodies.

Examination of infected HeLa cells by immunofluorescence microscopy with fluorescently labeled anti-phosphotyrosine antibodies or rhodamine-phalloidin showed that, unlike wild-type parental enteropathogenic *E. coli*, the espA mutant did not accumulate tyrosine phosphorylated proteins or cytoskeletal actin beneath the adherent microcolonies. However, phosphotyrosine and actin accumulation could be restored by using a strain carrying the espA gene on the plasmid pMSD2.

Immunofluorescence microscopy was performed as follows: HeLa cells which were seeded on round glass cover slips were infected with enteropathogenic *E. coli* or a mutant strain for three hours. The monolayers were then washed and fixed in 2.5% paraformaldehyde prior to staining for filamentous actin (using phalloidin-rhodamine) or with anti-phosphotyrosine antibodies with an appropriate secondary fluorescein conjugated antibody.

EXAMPLE 6

Characterization of Rabbit Enteropathogenic *E. coli* (RDEC-11 Secreted Virulence Proteins, EspA and EspB The purpose of this Example was to investigate the structure of EspA and EspB in rabbit enteropathogenic *E. coli* (RDEC-1). The espA and espA genes were cloned and their sequences were compared to those of enteropathogenic *E. coli* (SPEC). The EspA protein showed some similarity (88.5% identity). The EspB protein was heterogeneous in internal regions (69.8% identity), but was identical to one strain of enterohemorrhagic *E. coli* (EHEC).

Figure 3A:
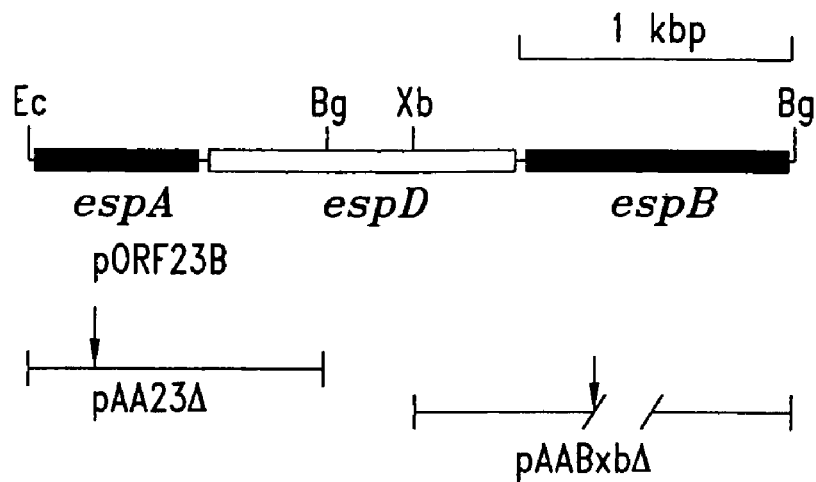
FIGS. 3A and 3B show a genetic map of the plasmids containing RDEC-1 (A) and enteropathogenic *Escherichia coli* (EPEC) (B) espA, espD, and espB genes. Arrows indicate positions that stop codon insertions were made in espA and espB (A), and the frame shift mutation engineered into the BglII site in espD (B). The 250 base pair deletion in espB is marked by //. Solid and clear boxes represent open reading frames and predicted open reading frames. Restriction enzymes are indicated as follows: Bam, BamFH; Ec, EcoRI; Bg, BglH; Xb, XbaI; Sa, UL
Figure 3B:
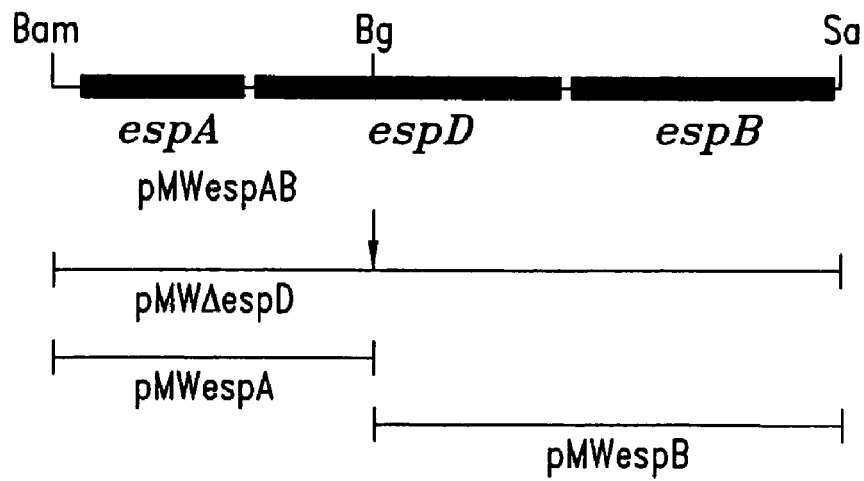

Cloning and sequence analysis of espA and espB genes was done as follows: The DNA fragment encoding RDEC-1 espA and espB was obtained by PCR from RDEC-1 chromosomal DNA using primers derived from the published sequence of enteropathogenic *E. coli*. Vent DNA polymerase was used for PCR to amplify chromosomal DNA from RDEC-1 and enteropathogenic *E. coli* strains. The PCR reaction was carried out for thirty cycles of denaturation at 94° C. for one minute, annealing at 55° C. for one minute, and elongation at 72° C. for two minutes. The resulting 4.3 kilobase pair product was ligated into the commercially available plasmid pBluescript and both strands were sequenced. DNA sequencing was done as follows: The 4.3 kilobase pair DNA fragment encoding the espA and espB genes was amplified by PCR using the primers AA01(+) and MS 11(−), and RDEC-1 chromosomal DNA as the DNA template. The resulting blunt end fragment was digested with SalI and cloned into the SalI-SmaI site of the commercially available plasmid pBluescript-H SK (+). The DNA sequence of RDEC-1 espA and both strands using the commercially available Taq DyeDeoxy kit. (FIGS. 3A and 3b)

Two open reading frames were found in the cloned region and these DNA sequences were similar to enteropathogenic *E. coli* espA and espB. The predicted molecular weight of RDEC-1 EspA (192 amino acids) was 23,533 dalton, and RDEC-1EspB (314 amino acids) was 33,219 dalton. RDEC-1 EspA was somewhat similar to that of enteropathogenic *E. coli* with 88.5% identity (FIGS. 4A–4D).

In an unexpected result, RDEC-1 EspB protein was identical to the recently reported EspB from enterohemorrhagic *E. coli* strain 413/89-1 serotype 026, which was originally isolated from a calf and also isolated from patients with hemolytic uraemic syndrome, although two nucleotide differences occurred at positions 12 (T to C) and 729 base pair (G to T). Furthermore, RDEC-1 EspB showed 70.3% enc. 69.8% identity respectively to that of enterohemorrhagic *E. coli* serotype 0157 and enteropathogenic *E. coli* strains. Small sequence deletions were found in RDEC-1 and enterohemorrhagic *E. coli* (serotype 026 and 0157) EspB at the same positions when compared to the enteropathogenic *E. coli* sequences (FIGS. 4A–D).

These results show that RDEC-1 encodes espA and espB genes, and that the predicted EspA polypeptide is highly conserved in RDEC-1 and enteropathogenic *E. coli*. However EspB is more similar to that of enterohemorrhagic *E. coli* rather than enteropathogenic *E. coli*. An open reading frame downstream (3') from espA showed similarity to enteropathogenic *E. coli* EspD, a secreted protein that modulates EspB secretion and is needed for triggering of host signal transduction pathways (EMBL GenBank data, Accession No. Y09228). These results show that espD is also located between espA and espB in RDEC-1.

EXAMPLE 7

Characterization of RDEC-1 EspA and EspB

The purpose of this Example was to investigate the function of EspA and EspB in rabbit enteropathogenic *E. coli* (RDEC-1). Mutations in RDEC-1 espA and espB revealed that the RDEC-I gene products are essential for triggering of host signal transduction pathways and invasion into HeLa cells. Complementation with plasmids containing enteropathogenic *E. coli* espA and espB into RDEC-1 mutant strains demonstrated that they were functionally interchangeable, although the enteropathogenic *E. coli* proteins mediated higher levels of invasion. Furthermore, maximal expression of RDEC-1 and enteropathogenic *E. coli* secreted proteins occurred at their respective host's body temperatures, which may contribute to lack of enteropathogenic *E. coli* infectivity in rabbits.

To confirm the role of RDEC-1 espA and espB in host epithelial signal transduction pathways, a non-polar stop codon mutation was engineered into espA and espB. Two suicide vectors were constructed and introduced into the RDEC-1 wild type strain by back conjugation. The resulting mutant strains, AAF001ΔA (EspA$^-$), AAF001ΔB (EspB$^-$), and double mutant strain AAF001ΔAB (EspA$^-$/EspB$^-$) were confirmed by BglII digestion.

The construction of the non-polar stop codon mutations in RDEC-1 espA and espB genes was performed as follows: The 2.7 kilobase pair DNA fragment of the Locus of Enterocyte Effacement encoding the espA and espB genes was amplified by PCR using the primers BK25(+) and MSll(−), and pORF123B as the DNA template. The resulting blunt end fragment was digested with EcoRI and cloned into the EcoRI-SmaI site of pBluescript II SK(+) vector to obtain pORF23B. A 1.1 kilobase pair EcoRI-BglII DNA fragment from pORF23B containing espA was cloned into the EcoRI-BamHI site of pBluescript II SK(+) to obtain pORF23.

To construct a non-polar mutation in espA, inverse PCR was carried out using the ΔespA(+) and ΔespA(−) primers which contain a BglII restriction site and a stop codon using circular pORF23 as a DNA template. The PCR product was then blunt end ligated to obtain pORF23Δ. The resulting plasmid contained a stop codon and a BglII site 235 base pair downstream (3') from the espA start codon, which was confirmed by DNA sequencing. The 1.1 kilobase pair SalI-SacI DNA fragment containing the espA mutation from pORF23A was inserted into the same sites of the suicide vector pCVD442, which contains the sacB gene for positive selection and an ampicillin resistance gene, to obtain pAA23Δ. The resulting plasmid was introduced into *E. coli* SM10λpir and back conjugated into RDEC-1 harboring pACYC184.

For the non-polar mutation in espB, inverse PCR was carried out using the ΔespB(+) and ΔespB(−) primers, and pBxb as a DNA template. pBxb contains the 1.4 kilobase pair XbaI fragment from pORF23B encoding espB cloned into the pBluescript vector. The resulting PCR product was self-ligated to obtain pBxbΔ that contained a stop codon and a BglII site introduced by the ΔespB(−) and ΔespB(+) primers. The resulting esp gene in pBXbΔ was deleted by 250 base pair, starting 154 base pair downstream (3') of the espB start codon. The 1.1 kilobase pair SalI-SacI site DNA fragment containing the espB mutation from pBxbA was inserted into the same site of the pCVD442 to obtain pAABxbΔ. The resulting plasmid was transformed into *E. coli* SM1Oλpir and back conjugated into RDEC-1 harboring pACYC184. To establish double mutations in espA and espB, pAABxbΔ was introduced into AAFOO1ΔA (EspA$^-$) strain. Three RDEC-1 non-polar mutant strains were confirmed by their phenotypes which maintain resistance to sucrose and chloramphenicol, and sensitivity to ampicillin. To confirm the stop codon insertions in espA and espB, chromosomal DNA was prepared from each mutant strain and PCR was performed with primers encompassing the esp genes. The resulting PCR products were digested with BglII to confirm the presence of this engineered restriction site. The mutant strains containing the stop codon in espA or/and espB were designated as AAFOO1ΔA (EspA$^-$), AAFOO1ΔAB (EspB$^-$) and AAF001ΔAB (EspA$^-$/EspB$^-$), respectively.

Mutations back to wild type ("back mutation") were made to confirm that suicide vectors do not affect respective flanking region or other loci. Two back mutant strains were obtained by bans conjugation of the suicide vectors pAA23 and pAABxb into AAF001ΔA (EspA⁻) and AAF001ΔB (EspB⁻) strains. The resulting back mutant strains, AAF003 and AAF004, were confirmed by PCR and BglII digestion. The construction of back mutations in EspA and EspB strains was done as follows: The 1.1 kilobase pair SalI-SacI DNA fragment from pORF23 containing espA was inserted into the SalI-SacI sites of pCVD442 to obtain pAA23. The 1.4 kilobase pair SalI-SacI fragment of pBxb was inserted into the SalI-SacI site of pCDD442 to obtain pAAFBxb. pAA23 and pAABxb were introduced into SMλpir and bans conjugated into AAF001AA and AAF001AB. The resulting back mutant strains were confirmed as described above and designated as AAF002 (EspA+) and AAF003 (EspB+).

The cloning of the enteropathogenic *E. coli* espA and espB genes was done as follows: The 2.8 kilobase pair DNA fragment encoding espA and espB was amplified by PCR using the primers EespA(+) and EespB(−) with enteropathogenic *E. coli* 2348/69 chromosomal DNA as the template. This fragment was digested with BamHI and SalI and introduced into the BamHI-SalI site of the low-copy vector pMW118 under control of the lacZ promoter, to obtain pMWespAB. pMWespAB was digested with BglII which has a restriction site in espD open reading frame, blunt ended with Klenow fragment, and then self-ligated to obtain pMW6espD. pMWespAB was also digested with BglII and BamHI, and then self ligated to obtain pMWespB. The PMWespAB was digested with BglII-SalI, and filled with Klenow Fragment, then self-ligated to obtain pMWespA.

The secretion profile of RDEC-1 and its mutant strains in tissue culture media was analyzed. Enteropathogenic *E. coli* secretes five proteins, 110 kilodalton (EspC), 40 kilodalton, 39 kilodalton, 37 kilodalton (EspB), and 25 kilodalton (EspA) in culture media. RDEC-1 showed a similar secretion profile, except it did not secrete a protein equivalent to EspC. EspC is not required for enteropathogenic *E. coli* induction of host signal transduction pathways. Although two secreted proteins (40 and 39 kilodalton) were difficult to resolve, these proteins could be resolved using different conditions of SDS-PAGE. RDEC-1 secreted two proteins with similar mobility to enteropathogenic *E. coli* EspA and EspB.

RDEC-1 secreted proteins were prepared as follows: Bacterial overnight cultures were diluted 1:100 into DMEM and incubated to an optical density of 1.0 at 600 nm (OD600). For RDEC-1 mutant strains containing enteropathogenic *E. coli* espA and espB recombinant plasmids, isopropylthiogalactoside (IPTG) was added in DMEM to induce transcription. Bacteria were removed by centrifugation (18,000×g, 10 minutes) and the supernatant precipitated by addition of 10% ice-cold trichloroacetic acid, and incubated on ice for one hour. After centrifugation, the pellets were resuspended in Laemmli sample buffer and analyzed by 12% SDS-PAGE.

Both EspA and EspB proteins cross-react to anti-enteropathogenic *E. coli* EspA and anti-enteropathogenic *E. coli* EspB antisera in Western immunoblots, indicating that RDEC-1 also secretes EspA and EspB proteins. Rabbit polyclonal antibodies against enteropathogenic *E. coli* EspA and EspB were used in Western blots.

Mutant strains AAF001ΔA, AAF001AB, and AAF001ΔAB lack secretion of EspA, EspB, and EspA/EspB proteins, respectively, as judged by their secretion profile and Western blot analysis. EspB, whose gene is located downstream (3') from espA, was still secreted in the mutant strain AAF00ΔA (EspA⁻), indicating that the stop codon insertion mutation does not affect downstream gene expression. These results also confirm that RDEC-1 EspA and EspB proteins are encoded by the sequences we designated as espA and espB. Furthermore, the two back mutant strains AAF002 and AAF003, that were originally derived from AAF001ΔA (EspA⁻) and AAF001ΔB (EspB⁻), now expressed the parental secreted proteins indicating that each non-polar mutation in AAF001ΔA and AAF001ΔB is as predicted, and does not affect downstream genes and other loci. Although the mobilities of RDEC-1 EspA and EspB in SDS-PAGE were slightly faster than that of enteropathogenic *E. coli*, the calculated molecular masses of RDEC-1 EspA and EspB were greater than that of enteropathogenic *E. coli*.

The amount of the other secreted proteins were decreased in the EspA⁻, EspB⁻, EspA⁻/EspB⁻ strains when compared to wild type RDEC-1 strain. Furthermore, the decrease of detectable secretion of the 40 kilodalton and 39 kilodalton proteins in the EspA⁻/EspB⁻ strain is greater than that found in EspA⁻ and EspB⁻ strains. Secretion of enteropathogenic *E. coli* proteins, except EspC, are mediated by a type III secretion system encoded by the sep cluster. It is possible that truncation of EspA or EspB by inserting a stop codon may interfere with this secretion pathway or feedback regulation of this system, thereby affecting secretion of the other type III dependent secreted proteins.

Esp proteins are needed for triggering of the host signal transduction pathway. Enteropathogenic *E. coli* EspA and EspB proteins induce host signal transduction pathways resulting in accumulation of tyrosine phosphorylated proteins, cytoskeletal actin, and other components beneath the adherent bacteria. To determine whether RDEC-1 EspA and EspB trigger these events in HeLa cells, cytoskeletal actin add tyrosine-phosphorylated proteins were stained with rhodamine-phallodin and fluorescently labelled anti-phosphotyrosine antibody. Although the level of accumulation of cytoskeletal actin and tyrosine-phosphorylated protein beneath the attached RDEC-1 is lower than that of enteropathogenic *E. coli*, these behaviors were indistinguishable to that of enteropathogenic *E. coli*. By contrast, RDEC-1 EspA⁻, EspB⁻-, and EspA⁻/EspB⁻ strains did not accumulate cytoskeletal actin or tyrosine-phosphorylated proteins beneath the attached bacteria. However, the back mutant strains AAF003 and AAF004 accumulated these proteins similar to the parental strains.

When plasmids containing enteropathogenic *E. coli* espA or espB or both were introduced into the RDEC-1 EspA⁻, EspB⁻, and EspA⁻/EspB⁻ strains, the accumulation of cytoskeletal actin and tyrosine-phosphorylated proteins was also restored. However, when the enteropathogenic *E. coli* EspA⁻ strain, which still secretes EspB, was coinfected with RDEC-1 EspB, induction of host signal transduction events were not restored. Enteropathogenic *E. coli* EspB also did not complement RDEC-1 EspA in coinfection experiment. Therefore, functionally EspA and EspB are similar in RDEC-1 and enteropathogenic *E. coli*. with respect to activating host signal transduction pathways, although both proteins need to be secreted by the same strain.

Tyrosine-phosphorylated Hp90 could be detected by immunoblotting when HeLa cells were infected with enteropathogenic *E. coli*. Tyrosine-phosphorylated Hp90 could not be detected with RDEC-1 infected cells, even though tyrosine phosphorylated proteins could be observed under adherent RDEC-1 bacterial cells by immunofluorescence.

Enterohemorrhagic *E. coli* does not induce tyrosine phosphorylation in HEp-2 and T84 cells as judged by immun ofluorescence microscopy. The sequencing results showed that RDEC-1 EspB is more similar to that of enterohemorrhagic *E. coli* than enteropathogenic *E. coli*. These results in this Example show that the lower accumulation of tyrosine-phosphorylated proteins during RDEC-1 infection is due to lower adherence efficiency of RDEC-1 because of differences in adhesion levels or heterogeneity of Esp proteins or both.

Adherence and invasion ability. Enteropathogenic *E. coli* EspA and EspB are not only involved in triggering of host signal transduction pathways, but also necessary for invasion in vitro. In order to investigate the role of RDEC-1 EspA and EspB in adherence and invasion, RDEC-1 esp mutant strains were compared to that of RDEC-1. The adherence ability of EspA⁻, EspB⁻, and EspA⁻/EspB⁻ strains were similar to that of the wild type RDEC-1 strain, indicating that adherence is independent of EspA and EspB expression. Although the invasive ability of wild type RDEC-1 was about ninety times lower than that of enteropathogenic *E. coli*, this ability was further decreased in the mutant strains EspA⁻, EspB⁻, and EspA⁻/EspB⁻. However, invasion was restored by back mutation strains AAF002 and AAF003. These results show that RDEC-I invasion ability depends upon EspA and EspB.

To determine the ability of enteropathogenic *E. coli* EspA and EspB to complement the RDEC-1 mutants, various plasmids containing the enteropathogenic *E. coli* espA and espB genes were introduced into the RDEC-I mutant strains, and invasion efficiencies compared to that of wild type RDEC-I strain. Interestingly, the invasion levels of AAF001ΔAB (RDEC-1 EspA⁻/EspB⁻) harboring pMWespAB (EPEC EspA+/EspB+) was four times greater than that of wild type RDEC-1, even though the amount of secreted enteropathogenic *E. coli* EspA and EspB in AAF001 ΔAB strain was lower than that normally found in RDEC-1. Therefore, the different invasion levels observed between RDEC-I and enteropathogenic *E. coli* strains in HeLa cells can be attributed to the Esp proteins, and enteropathogenic *E. coli* EspA and EspB are more efficient at mediating invasion in this tissue culture model. Homology comparisons showed that EspA was highly conserved in RDEC-I and enteropathogenic *E. coli*, but EspB was more heterogeneous, showing that the difference of invasive abilities between RDEC-1 and enteropathogenic *E. coli* may be due to the EspB protein. Interestingly, enterohemorrhagic *E. coli* 0157 adheres to, but does not invade into human ileocecal (HCT-8) epithelial cells. RDEC-1 EspB was more similar to that of enterohemorrhagic *E. coli* rather than enteropathogenic *E. coli*, perhaps emphasizing the role of EspB in invasion. These findings strongly support that Esp heterogeneity affects the invasive ability of enteropathogenic *E. coli*, RDEC-1, and enterohemorrhagic *E. coli*.

EspD mutant affects EspA and EspB secretion. Enteropathogenic *E. coli* contains an open reading frame, espD, located between espA and espB. To confirm the role of the espD product in secretion, the plasmid pMWespD encoding enteropathogenic *E. coli* espA, ΔespD (frame shift mutation at the BgIII site), and espD was constructed and introduced into the RDEC-1 double mutant strain, AAF001AAB. The amount of enteropathogenic *E. coli* EspA and EspB secreted proteins in AAFOOIAAB [pMWespD] was lower than that in AAF001AAB [pMWespAB], which contains fragment encoding intact enteropathogenic *E. coli* espA, espD, and espB genes. Furthermore invasion ability was also decreased. These results show that disruption of espD affects secretion of enteropathogenic *E. coli* EspA and EspB proteins. In this Example, we showed that mutations in espA and/or espB also reduced the amount of the other secreted proteins, probably due to their truncated products. Secretion levels were more decreased in espA and espB double mutants when compared with espA or espB mutants. Thus, truncated enteropathogenic *E. coli* EspD may affect the secretion of EspA and EspB in AAF001AAB [pMW6espD] due to interference in type III secretion system. Whether or not EspD is directly involved in this secretion system is still unclear.

Enteropathogenic *E. coli* and RDEC-1 secreted proteins are tightly controlled by temperatures, which correspond to their relevant host body temperatures. Temperature regulates the expression of enteropathogenic *E. coli* and enterohemorrhagic *E. coli* 413/89-1 secreted proteins. EspB expression was greatly increased when the temperature was shifted from 20° C. to 37° C. Because EspA and EspB proteins are regulated by appropriate host body temperatures, wild type enteropathogenic *E. coli* and RDEC-1 strains were inoculated into DMEM and the secreted proteins were prepared following incubation at various temperatures, then analyzed by SDS-PAGE. Expression of enteropathogenic *E. coli* secreted proteins were visible at 33° C. and reached maximal secretion level at 36° C. Expression was decreased at 39° C., and no secreted proteins were seen at 42° C. In contrast, maximal expression of RDEC-1 secreted proteins occurred at 39° C. and these proteins were still expressed at 42° C. These results show that the maximal expression of Esp proteins in enteropathogenic *E. coli* and RDEC-1 are triggered by their relevant host's body temperature, human (37° C.) and rabbit (39° C.).

In conclusion, both proteins were needed to trigger host signal transduction pathways and invasion. Complementation experiments using enteropathogenic *E. coli* esp genes revealed that host signal transduction events triggered by RDEC-I and enteropathogenic *E. coli* appear to be mediated by the same secreted proteins. Finally, optimal expression of RDEC-1 and enteropathogenic *E. coli* secreted proteins correlated with their natural host's body temperature. This explains their strict host specificity and the lack of enteropathogenic *E. coli* infection in rabbits or other animals. Animal infection studies using RDEC-1 espA and espB strains will provide information about the role of these secreted proteins in virulence, and may possibly be useful for vaccine studies.

EXAMPLE 8

Two Rabbit Enteropathogenic *E. coli* (RDEC-1) Secreted Proteins, EspA and EspB, Are Virulence Factors The purpose of this Example is to demonstrate the role of EspA and EspB proteins in pathogenesis. To investigate the role of these proteins in virulence, mutations in espA and espB were constructed in the rabbit enteropathogenic *E. coli* strain, RDEC-1.

RDEC-1 and its espA and espB mutant strains were inoculated by the orogastric route into young rabbits. Most RDEC-1 was found in the cecum and colon one week postinfection. However, the number of either mutant strain was greatly decreased in these tissues compared to the parent strain. RDEC-1 adhered specifically to the sacculus rotundas (follicle associated epithelium) and bacterial colonization was also observed in the cecum, indicating that the sacculus rotundas in the cecum is an important colonization site for this pathogen. The adherence levels of the EspA⁻ and EspB⁻ strains to the sacculus rotundas were 70 and 8000 times less than that of parent strain. These results show that the adherence ability and tissue tropism of RDEC-1 are dependent on the two Esp secreted proteins. Furthermore, EspB appears to play a more critical role than EspA in bacterial colonization and pathogenesis. This is the first demonstration that the enteropathogenic *E. coli* secreted proteins, EspA and EspB, which are involved in triggering of host cell signal transduction pathways, are also needed for colonization and virulence.

Animal infections were performed as follows: Overnight bacterial cultures were collected by centrifugation and resuspended in one ml of phosphate-buffered saline. New Zealand white rabbits (weight 1.0 to 1.6 kg) were fasted overnight, then five ml of 2.5% sterile sodium bicarbonate and one ml of RDEC-1 or espA or espB strains ($2.5 \times 10^{10}$) were inoculated into the stomach using orogastric tubes. The same dosage of bacteria was inoculated into each rabbit the following day.

Clinical assessments were performed as follows: Each rabbit was weighed daily and fecal shedding of bacteria were collected by rectal swabs and from stool pellets. Rectal swabs were rolled over one half of the surface of MacConkey plates containing nalidixic acid. Five stool pellets or same amount of liquid stool were collected from each rabbit and resuspended in three ml phosphate-buffered saline and 0.1 ml of each stoolsuspension was plated onto MacConkey plate containing nalidixic acid. The growth of nalidixic resistant colonies was scored as follows: 0, no growth; 1, widely spaced colonies; 2, closely spaced colonies; 3, confluent growth of colonies.

Sampling and preparation of tissue were performed as follows: Tissues were excised immediately following sacrifice by intravenous injection of ketamine and overdosing with sodium phenobarbital.

The amount of bacterial colonization in intestinal tissues was assayed as follows: The intestinal segments (10 cm), except cecum, were doubly ligated at their proximal and distal ends, and dissected between the double ligated parts, then flushed with 10 ml of ice-cold phosphate-buffered saline. One gram of viscous contents from the cecum was added to 9 ml phosphate-buffered saline. The resulting phosphate-buffered saline suspensions were diluted and plated on MacConkey plates containing nalidixic acid.

The amount of bacterial adherence to intestinal tissues was assayed as follows: Tissue samples were excised using a nine mm diameter cork punch, washed three times with phosphate-buffered saline, added to two ml of ice-cold phosphate-buffered saline, and homogenized with a homogenizer, then serial diluted samples were plated onto MacConkey plates. The numbers of bacteria adherent to each tissue per square centimeter were calculated as follows: $CFU/cm2$=the bacterial number/plate×dilution factor×2 ml/−0.452.

EXAMPLE 9

Development of an Assay to Screen for Inhibitors of Bacterial Type III Secretion The purpose of this Example is to provide an assay to screen for inhibitors of bacterial type III secretion.

A polynucleotide encoding the EspA polypeptide is fused to several well known molecules, including a HSV tag. The gene fusion is still secreted out of enteropathogenic *E. coli*. A plasmid contains the genetic region of espA that encodes the amino-terminal portion of EspA (needed to mediate type III secretion) fused to a Herpes Simplex Virus (HSV) sequence that encodes a sequence tag to which commercial antibodies are available. This plasmid is transformed into a strain that contains an espA mutation yet still secretes the other enteropathogenic *E. coli*-secreted proteins that use the type III secretion system. The supernatant of organisms containing these fusions is collected, added to an ELISA plate, followed by standard ELISA. A calorimetric readout indicates the fusion protein is secreted.

This plasmid is also transformed into a strain which is defective for type III secretion (i.e., a negative control). When the fusion protein is expressed in this strain, the fusion protein is expressed but not secreted. ELISA results with this mutant confirm that it is not secreted.

Thus an easy ELISA assay to look at secretion is provided. This assay is simple, and requires no special technology. It is also economical, because no expensive reagents are needed. It is automated and used to screen reagents to identify inhibitors of bacterial type III secretion.

To assay for secretion, bacteria are grown standing overnight in tissue culture fluid in the presence of compounds to be tested. These conditions yield enteropathogenic *E. coli*-mediated secretion. The following day, bacteria are removed by centrifugation, and the supernatant placed into wells of a 96 well microtiter plate. A standard ELISA is performed on the supernatants. If the compound being tested is bactericidal, the bacteria do not grow overnight.

A polynucleotide encoding another polypeptide secreted by enteropathogenic *E. coli* is fused to several well known molecules. A polynucleotide encoding EspB polypeptide was fused a HSV tag, to which commercial antibodies are available. The gene fusion was still secreted out of enteropathogenic *E. coli*. This plasmid was transformed into a strain that contained an espA mutation yet still secretes the other enteropathogenic *E. coli*-secreted proteins that use the type III secretion system. The supernatant of organisms containing these fusions is collected, added to an ELISA plate, followed by standard ELISA technology with, for example, anti-HSV antibodies. This screen was used to assay plant extracts from medically important plants. Dilutions of $1/200$–$1/1000$ (about 250 µg/ml) are appropriate. Promising compounds are rescreened in the ELISA secretion assay to check for reproducibility.

Although the invention has been described with reference to the presently preferred embodiments, it should be understood that various modifications can be made without departing from the spirit of the invention. Accordingly, the invention is limited only by the following claims.

What is claimed:

1. A method for detecting EspA polypeptide in a sample, comprising:

a) contacting the sample with an isolated antibody specific for an EspA polypeptide, wherein the polypeptide is a secreted protein from enteropathogenic *E. coli* and comprises an amino acid sequence as set forth in SEQ ID NO:2 or SEQ ID NO:4, b) detecting binding of the antibody to EspA polypeptide, wherein binding is indicative of the presence of EspA polypeptide in the sample.

2. The method of claim 1, wherein the sample is tissue.

3. The method of claim 1, wherein the sample is a biological fluid.

4. The method of claim 1, wherein the presence of EspA polypeptide in the sample is indicative of infection by enteropathogenic *E. coli*.

* * * * *